United States Patent
Kutsuna et al.

(10) Patent No.: US 9,396,534 B2
(45) Date of Patent: Jul. 19, 2016

(54) MEDICAL IMAGE PROCESSING APPARATUS AND MEDICAL IMAGE PROCESSING SYSTEM

(71) Applicant: Toshiba Medical Systems Corporation, Otawara-shi (JP)

(72) Inventors: Yasunari Kutsuna, Nasushiobara (JP); Kousuke Sakaue, Nasushiobara (JP); Masashi Yoshida, Nasushiobara (JP); Shigeyuki Ishii, Nasushiobara (JP); Satoshi Ikeda, Yaita (JP); Hitoshi Yamagata, Otawara (JP); Takashi Masuzawa, Otawara (JP); Naoki Sugiyama, Otawara (JP); Muneyasu Kazuno, Nasushiobara (JP); Satoshi Sugisawa, Utsunomiya (JP); Junichi Tashiro, Otawara (JP); Maiko Tezuka, Nasushiobara (JP); Maki Minakuchi, Utsunomiya (JP); Yosuke Yanagida, Otawara (JP); Jyunichi Yoshida, Nasushiobara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/672,440

(22) Filed: Mar. 30, 2015

(65) Prior Publication Data
US 2015/0279061 A1  Oct. 1, 2015

(30) Foreign Application Priority Data
Mar. 31, 2014  (JP) .................. 2014-073440

(51) Int. Cl.
*G06K 9/00* (2006.01)
*G06T 7/00* (2006.01)
*G06T 11/00* (2006.01)

(52) U.S. Cl.
CPC ............. *G06T 7/0012* (2013.01); *G06T 7/0081* (2013.01); *G06T 11/003* (2013.01); *G06T 2200/24* (2013.01); *G06T 2207/10004* (2013.01); *G06T 2207/10072* (2013.01); *G06T 2207/30004* (2013.01); *G06T 2207/30196* (2013.01); *G06T 2211/424* (2013.01)

(58) Field of Classification Search
None
See application file for complete search history.

(56) References Cited

U.S. PATENT DOCUMENTS

| | | | | | |
|---|---|---|---|---|---|
| 2002/0193676 | A1* | 12/2002 | Bodicker | ............ | G06F 17/3028 600/407 |
| 2005/0201607 | A1* | 9/2005 | Sato | ......................... | G06T 5/50 382/131 |

(Continued)

FOREIGN PATENT DOCUMENTS

| JP | 2008-194456 | 8/2008 |
|---|---|---|
| JP | 2009-219655 | 10/2009 |

*Primary Examiner* — Shervin Nakhjavan
(74) *Attorney, Agent, or Firm* — Oblon, McClelland, Maier & Neustadt, L.L.P.

(57) ABSTRACT

A medical image processing apparatus displaying at least one medical image obtained by imaging an object comprises: processing circuitry configured to detect a position of a characteristic local structure of a human body from the medical image, to determine check information indicating the local structure which should be checked; and to determine whether or not the local structure which should be checked indicated in the check information has been diagnostically read based on the position of the local structure detected from the medical image; and a display configured to display a determination result.

18 Claims, 18 Drawing Sheets

(56) References Cited

U.S. PATENT DOCUMENTS

| | | | | |
|---|---|---|---|---|
| 2007/0129609 A1* | 6/2007 | Kawasaki | G06F 19/3418 | 600/300 |
| 2012/0130743 A1* | 5/2012 | Gotthardt | G06Q 50/24 | 705/3 |
| 2013/0184537 A1* | 7/2013 | Konuma | A61B 5/0033 | 600/300 |
| 2014/0221836 A1* | 8/2014 | Takeda | A61B 8/463 | 600/443 |
| 2014/0314287 A1* | 10/2014 | Doi | G06F 19/321 | 382/128 |
| 2015/0278445 A1* | 10/2015 | Miura | G06F 19/321 | 705/2 |
| 2016/0063699 A1* | 3/2016 | Gustafson | G06T 7/0012 | 715/738 |

* cited by examiner

FIG. 5A

| HEAD, NECK |
|---|
| ANTERIOR ARCH (TUBERCLE) OF ATLAS (CERVICAL VERTEBRA I) |
| SUPERIOR TIP OF DENS / PEG (CERVICAL VERTEBRA II) |
| SUPERIOR ASPECT OF RIGHT EYE GLOBE |
| SUPERIOR ASPECT OF LEFT EYE GLOBE |
| CENTER OF RIGHT EYE GLOBE |
| CENTER OF LEFT EYE GLOBE |
| ⋮ |

FIG. 5B

| CHEST |
|---|
| BIFURCATION OF TRACHEA |
| APEX OF RIGHT LUNG |
| APEX OF LEFT LUNG |
| INFERIOR ANGLE OF RIGHT SCAPULA |
| INFERIOR ANGLE OF LEFT SCAPULA |
| START OF LEFT SUBCLAVIAN ARTERY (BRANCHING OFF AORTIC ARCH) |
| ⋮ |

FIG. 5C

| ABDOMEN |
|---|
| SUPERIOR POLE OF RIGHT KIDNEY |
| SUPERIOR POLE OF LEFT KIDNEY |
| INFERIOR POLE OF RIGHT KIDNEY |
| INFERIOR POLE OF LEFT KIDNEY |
| HEAD OF PANCREAS |
| TIP OF TAIL OF PANCREAS |
| ⋮ |

FIG. 5D

| LOWER LIMBS |
|---|
| LATERAL EPICONDYLE OF RIGHT FEMUR |
| MEDIAL EPICONDYLE OF RIGHT FEMUR |
| LATERAL EPICONDYLE OF LEFT FEMUR |
| MEDIAL EPICONDYLE OF LEFT FEMUR |
| LATERAL CONDYLE OF RIGHT TIBIA |
| MEDIAL CONDYLE OF RIGHT TIBIA |
| ⋮ |

| IDENTIFIER | NAME | RELIABILITY | PART | BODY TISSUE | PATIENT COORDINATE SYSTEM | | |
|---|---|---|---|---|---|---|---|
| | | | | | X | Y | Z |
| ABD025.C | CENTER OF BODY OF L5 | 0.87 | ABDOMEN | SKELETAL SYSTEM | -3.1 | 23.4 | 90.0 |
| ABD032.C | SUPERIOR ASPECT OF RIGHT ILIAC SPINE | 0.82 | ABDOMEN | SKELETAL SYSTEM | -11.1 | -54.4 | 84.1 |
| ABD039.C | SUPERIOR ASPECT OF LEFT ILIAC SPINE | 0.83 | ABDOMEN | SKELETAL SYSTEM | -3.0 | 30.0 | 104.0 |
| ⋮ | ⋮ | ⋮ | ⋮ | ⋮ | ⋮ | ⋮ | ⋮ |

FIG. 7A

INSPECTION PURPOSE TABLE

| INSPECTION PURPOSE | CHECK TARGET POSITION |
|---|---|
| INSPECTION PURPOSE A | AL1, AL3, AL5, AL7 |
| INSPECTION PURPOSE B | AL2, AL4, AL6 |
| INSPECTION PURPOSE C | AL1, AL2, AL3, AL4, AL5 |
| ⋮ | ⋮ |

FIG. 7B

MEDICAL HISTORY TABLE

| MEDICAL HISTORY | CHECK TARGET POSITION |
|---|---|
| MEDICAL HISTORY A | AL3, AL4, AL5, AL8, AL9 |
| MEDICAL HISTORY B | AL2, AL3, AL8 |
| MEDICAL HISTORY C | AL1, AL2, AL3, AL6 |
| ⋮ | ⋮ |

FIG. 7C

ASSUMED DISEASE NAME TABLE

| ASSUMED DISEASE NAME | CHECK TARGET POSITION |
|---|---|
| DISEASE NAME A | AL5, AL6, AL7 |
| DISEASE NAME B | AL2, AL3, AL5, AL6 |
| DISEASE NAME C | AL1, AL5 |
| ⋮ | ⋮ |

FIG. 7D

PRIMARY SITE TABLE

| PRIMARY SITE | DISEASE NAME | CHECK TARGET POSITION (METASTASIS DESTINATION/ CONCURRENCE SPOT) |
|---|---|---|
| AL1 | DISEASE NAME A | AL9 |
| AL1 | DISEASE NAME B | AL5, AL6, AL7 |
| AL1 | DISEASE NAME C | AL7, AL8 |
| ⋮ | ⋮ | ⋮ |

| CHECK TARGET POSITION | SLICE NO. | PRESENCE OF DISPLAY | CHECK RESULT |
|---|---|---|---|
| AL1 | 2 | NO | NA |
| | 3 | NO | |
| | 4 | YES | |
| | 5 | YES | |
| AL2 | 4 | YES | NA |
| | 5 | YES | |
| | 6 | NO | |
| | 7 | NO | |
| ⋮ | ⋮ | ⋮ | ⋮ |

| CHECK TARGET POSITION | COORDINATE | PRESENCE OF DISPLAY | CHECK RESULT |
|---|---|---|---|
| AL1 | X1, Y1 | YES | COMPLETED |
| | X2, Y2 | YES | |
| | X3, Y3 | YES | |
| AL2 | X4, Y4 | NO | NA |
| | X5, Y5 | NO | |
| ⋮ | ⋮ | ⋮ | ⋮ |

| KEY IMAGE ANATOMICAL POSITION |
|---|
| BIFURCATION OF TRACHEA |
| APEX OF RIGHT LUNG |
| APEX OF LEFT LUNG |
| INFERIOR ANGLE OF RIGHT SCAPULA |

| CHECK TARGET POSITION | SLICE NO. | PRESENCE OF DISPLAY | DISPLAY START TIME (HOUR:MINUTE:SECOND) | DISPLAY CHANGE TIME (HOUR:MINUTE:SECOND) | CHECK RESULT | CHECK COMPLETION TIME (HOUR:MINUTE:SECOND) |
|---|---|---|---|---|---|---|
| AL1 | 2 | YES | 15:16:20 | 15:17:40 | COMPLETED | 15:30:40 |
| | 3 | YES | 15:17:40 | 15:18:00 | | |
| | 4 | YES | 15:18:00 | 15:19:10 | | |
| | 5 | YES | 15:19:10 | 15:19:55 | | |
| AL2 | 4 | YES | 15:18:00 | 15:19:10 | NA | |
| | 5 | YES | 15:19:10 | 15:19:55 | | |
| | 6 | NO | | | | |
| | 7 | NO | | | | |
| ... | ... | ... | ... | ... | ... | ... |

FIG. 15

| CHECK TARGET POSITION | CHECK RESULT |
|---|---|
| AL1 | |
| AL2 | |
| AL3 | |
| AL5 | |
| AL7 | |
| AL8 | |

FIG. 17A

| CHECK TARGET POSITION | CHECK RESULT |
|---|---|
| AL1 | FAVORABLE |
| AL2 | NEEDS CARE |
| AL3 | INSUFFICIENT |
| AL5 | INSUFFICIENT |
| AL7 | NEEDS CARE |
| AL8 | INSUFFICIENT |

FIG. 17B

MEDICAL IMAGE PROCESSING APPARATUS AND MEDICAL IMAGE PROCESSING SYSTEM

CROSS-REFERENCE TO RELATED APPLICATION

This application is based upon and claims the benefit of priority from Japanese Patent Application No. 2014-73440, filed on Mar. 31, 2014, the entire contents of which are incorporated herein by reference.

FIELD

An embodiment as an aspect of the present invention relates to a medical image processing apparatus and a medical image processing system.

BACKGROUND

Various inspection apparatus (hereinafter referred to as modality apparatus) used in image diagnosis can conduct inspections in the body in a low invasive manner and are indispensable in current medical practice. With improvement of performances of the modality apparatus, a good-quality image with high resolution can be now acquired, and accurate and precise inspections have become possible in image diagnosis. There are many imaging methods according to the modality apparatus such as an X-ray CT (Computed Tomography) apparatus capable of acquiring three-dimensional information of an internal tissue of an object with high resolution and an MRI (Magnetic Resonance Imaging) apparatus capable of MR Angiography (MRA) in which fresh blood without a contrast agent mixed is imaged, for example. Digitalization of medical images have progressed and an HIS (Hospital Information System) which is an ordering system for processing an inspection request from a doctor through an electronic network, an RIS (Radiology Information System), a PACS (Picture Archiving and Communication Systems) for storing images acquired by the modality apparatus as electronic data and the like have been developed.

As described above, development of the modality apparatus have enabled easy and detailed in-vivo observation. In contrast, an attainable data amount has become huge, and in many modality apparatus, data is acquired in a format of volume data constituted by a plurality of images. A data amount of the volume data amounts to several thousand shots when an image of a whole body is picked up, and a burden on a diagnostic reading doctor or the like by using such data so as to make diagnostic reading is large. Diagnostic reading is an important work in diagnosing a disease and determination of treatment policies and early detection is in demand, but analysis of a large amount of medical images and determination at an early stage is not easy. Thus, as an invention for supporting image diagnosis, a medical image processing apparatus for specifying an anatomical part by using a segmentation technology or the like and for determining an abnormal region and its malignancy and an image analyzing apparatus for determining a positional correspondence relation in images acquired in two different inspections by a structure having periodicity such as a spine are provided.

Diagnostic reading and diagnosis require accuracy, and to make high-quality diagnosis, abnormal parts and treatment parts need to be accurately grasped in the acquired medical images. However, diagnostic reading of anatomical parts from medical images requires skilled techniques and knowledge. Thus, technologies for expressing/constructing anatomical positions of a human body by using mathematical methods have been provided and studied.

The anatomical position refers to a position in a pathognomonic local structure (hereinafter referred to simply as a local structure) of a human body playing an important role in understanding the medical images and makes a mark when the human body is mapped anatomically. For example, an anterior arch (node) in a first cervical spine in a head, a bifurcation of trachea in a chest or an upper pole of right kidney in an abdomen corresponds to the local structure. A position (anatomical position) of this local structure is automatically detected from the medical images acquired by the modality apparatus such as an X-ray CT apparatus and an MRI apparatus by general image analysis, a pattern recognition technique and the like.

Diagnostic reading of medical images performed when creating a diagnostic reading report needs to be performed extensively so as not to miss finding. That is, all the slice images acquired in the number of several hundreds to thousands per patient in one session of imaging need to be checked. However, parts and local structures not relating to an inspection purpose are included in the slice images acquired in the inspection. Diagnostic reading doctors and the like need to analyze such large amount of medical image data, and whether or not parts and local structures which really need to be checked in diagnostic reading have been checked cannot be grasped easily. In diseases in which abnormality appears in a plurality of organs such as cancers and immune diseases, the relating parts or local structures might be missed by mistake such as mere lack of knowledge or forgetfulness.

Thus, a medical image processing apparatus capable of checking whether or not the parts and local structures requiring check in an inspection or diagnosis have been diagnostically read based on a position (anatomical position) of the above-described local structures is in demand.

BRIEF DESCRIPTION OF THE DRAWINGS

In accompanying drawings,

FIGS. 5A to 5D are views for explaining types of the local structures.

FIGS. 7A to 7D are views for explaining an example of the check item table of the medical image processing apparatus according to this embodiment.

FIG. 15 is a view for explaining diagnostic reading determination time of the medical image processing apparatus according to the embodiment.

FIGS. 17A and 17B are views for explaining other display examples of the diagnostic reading check situation of the medical image processing apparatus according to the embodiment.

DETAILED DESCRIPTION

A medical image processing apparatus according to this embodiment is a apparatus provided with a function for displaying a medical image such as a diagnostic reading report creating apparatus, a medical image observing apparatus (image viewer) and the like. Embodiments of the medical image processing apparatus will be described below by referring to the attached drawings.

First Embodiment

The medical image processing apparatus according to an embodiment is a medical image processing apparatus for displaying at least one medical image obtained by imaging an object and includes a position detecting portion for detecting a position of a characteristic local structure of a human body from the medical image, a check information determining portion for determining check information indicating a local structure which should be checked, a diagnostic reading determining portion for determining whether or not the local structure which should be checked indicated in the check information has been diagnostically read based on the position of the local structure detected from the medical image, and a display portion for displaying a determination result in the diagnostic reading determining portion.

(1) Configuration

Figure 1:
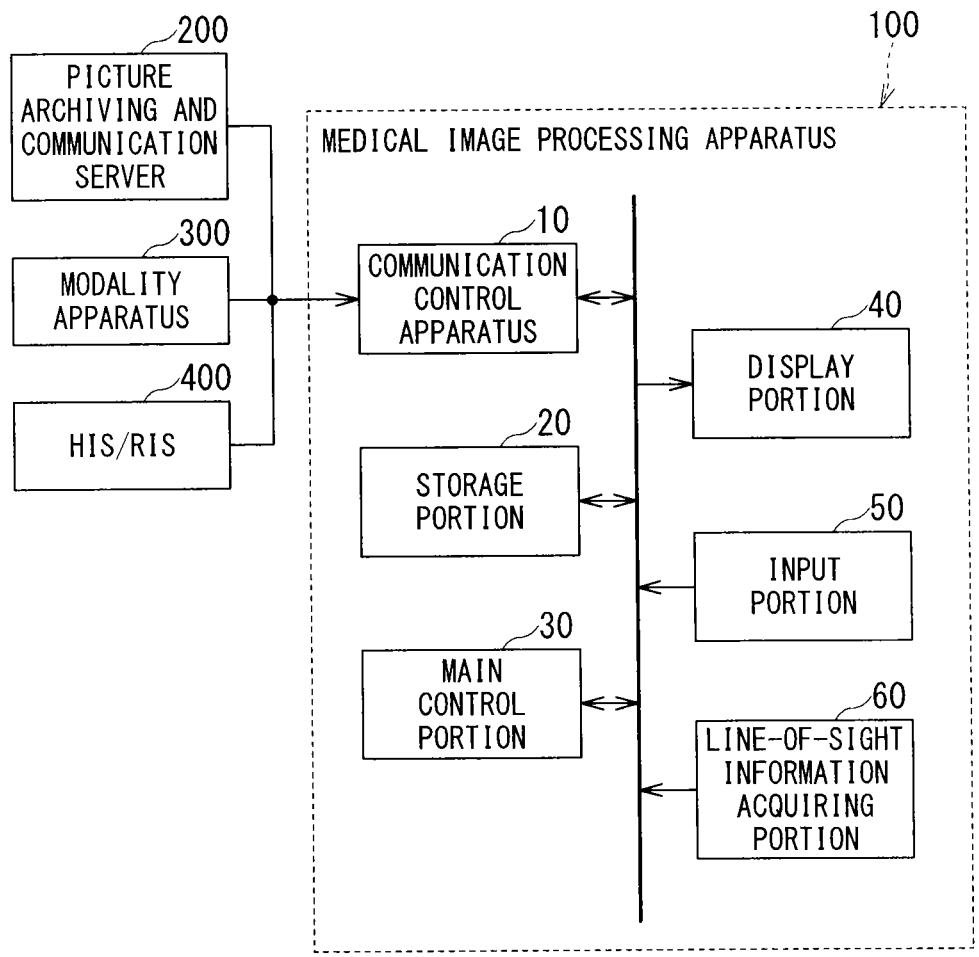
FIG. 1 is a conceptual configuration view illustrating an example of a medical image processing apparatus according to the embodiment.

FIG. 1 is a conceptual configuration view illustrating an example of a medical image processing apparatus 100 according to the embodiment. As illustrated in FIG. 1, the medical image processing apparatus 100 is configured by including a communication control apparatus 10, a storage portion 20 (memory circuitry 20), a main control portion 30, a display portion 40 (display 40), an input device 50, and a line-of-sight information acquiring portion 60. The medical image processing apparatus 100 is connected to a medical picture archiving and communication server 200, a modality apparatus 300, and a HIS/RIS 400 through the communication control apparatus 10 via an electronic network. The communication control apparatus 10 implements various communication protocols according to the network form. The electronic network here means an entire information communication network using IT technology and includes a hospital backbone LAN, a wireless/wired LAN, the Internet and the like and also includes a telephone communication line network, an optical fiber communication network, a cable communication network, and satellite communication network and the like. The medical image processing apparatus 100 acquires inspection data from the medical picture archiving and communication server 200 or the modality apparatus 300 via the electronic network.

The medical picture archiving and communication server 200, the HIS/RIS 400, and the medical image processing apparatus 100 may be constituted as a medical image processing system on a cloud. In this case, the medical image processing apparatus 100 of the medical image processing system can acquire medical images from the medical picture archiving and communication server 200 and the modality apparatus 300 via the network. As a result, the medical image processing apparatus 100 of the medical image processing system can create a diagnostic reading report.

The modality apparatus 300 includes various medical image pickup apparatus such as an X-ray CT (Computed Tomography) apparatus, an MRI (Magnetic Resonance Imaging) apparatus, a PET (Positron Emission Tomography) apparatus or an ultrasonic diagnosis apparatus. The medical image processing apparatus 100 receives volume data constituted by a plurality of slice images via the electronic network.

The medical image processing apparatus 100 is connected to the HIS/RIS 400. The HIS/RIS 400 is a system for processing an inspection request and the like called an inspection order created by a doctor or the like. A patient ID for uniquely identifying a patient or patient information such as a patient name, sex, body build, age and the like of the patient and study information such as inspection types, inspection purposes, types of the modality apparatus and the like can be acquired from the HIS/RIS 400 via the electronic network.

When a program stored in the storage portion 20 is executed by a processor of the main control portion 30, the medical image processing apparatus 100 performs detection of a position (anatomical position) of a local structure and creation of diagnostic reading check information for volume data or determination of a diagnostic reading situation based on the diagnostic reading check information and the like. In the description below, a position in a patient coordinate system of the local structure detected from the medical image is referred to as an anatomical position as appropriate.

The storage portion 20 is constituted by a storage medium including a RAM and ROM and has a configuration including a storage medium such as a magnetic or optical storage medium or a semiconductor memory which is readable by the main control portion 30 and may be configured so that a part of or the whole of the program and data in these storage mediums is downloaded via the electronic network. Detection of the anatomical position performed in the medical image processing apparatus 100 may be performed by using a program or data stored in the storage portion 20 in advance or by using data stored in an external storage apparatus or the like through the communication control apparatus 10 or may be executed by a program stored in an external storage apparatus and the like.

The display portion 40 is constituted by a general display apparatus such as a liquid crystal display, an OLED (Organic Light Emitting Diode) display and the like, for example, and displays an image in accordance with control of the main control portion 30.

The input device 50 is constituted by general input apparatus such as a keyboard, a touch panel, ten keys, a mouse and the like, for example. The input device 50 may include an input apparatus corresponding to an input by sound such as a microphone. The input device 50 outputs an input signal corresponding to operations such as selection of a medical image by a user or an input of diagnostic reading check information to the main control portion 30.

The line-of-sight information acquiring portion 60 is constituted by a general video camera provided with a semiconductor image pickup element such as a CCD (Charge Coupled Apparatus) image sensor, a CMOS (Complementary Metal Oxide Semiconductor) image sensor and the like and is also constituted by a Web camera built in a personal computer or a mobile apparatus and a network camera and the like. The line-of-sight information acquiring portion 60 includes a configuration of a storage medium or the like that can be read by the main control portion 30 of the medical image processing apparatus 100 which digitally converts the acquired line-of-sight information and stores the converted digital data in addition to the above-described configuration as a video camera.

Figure 2:
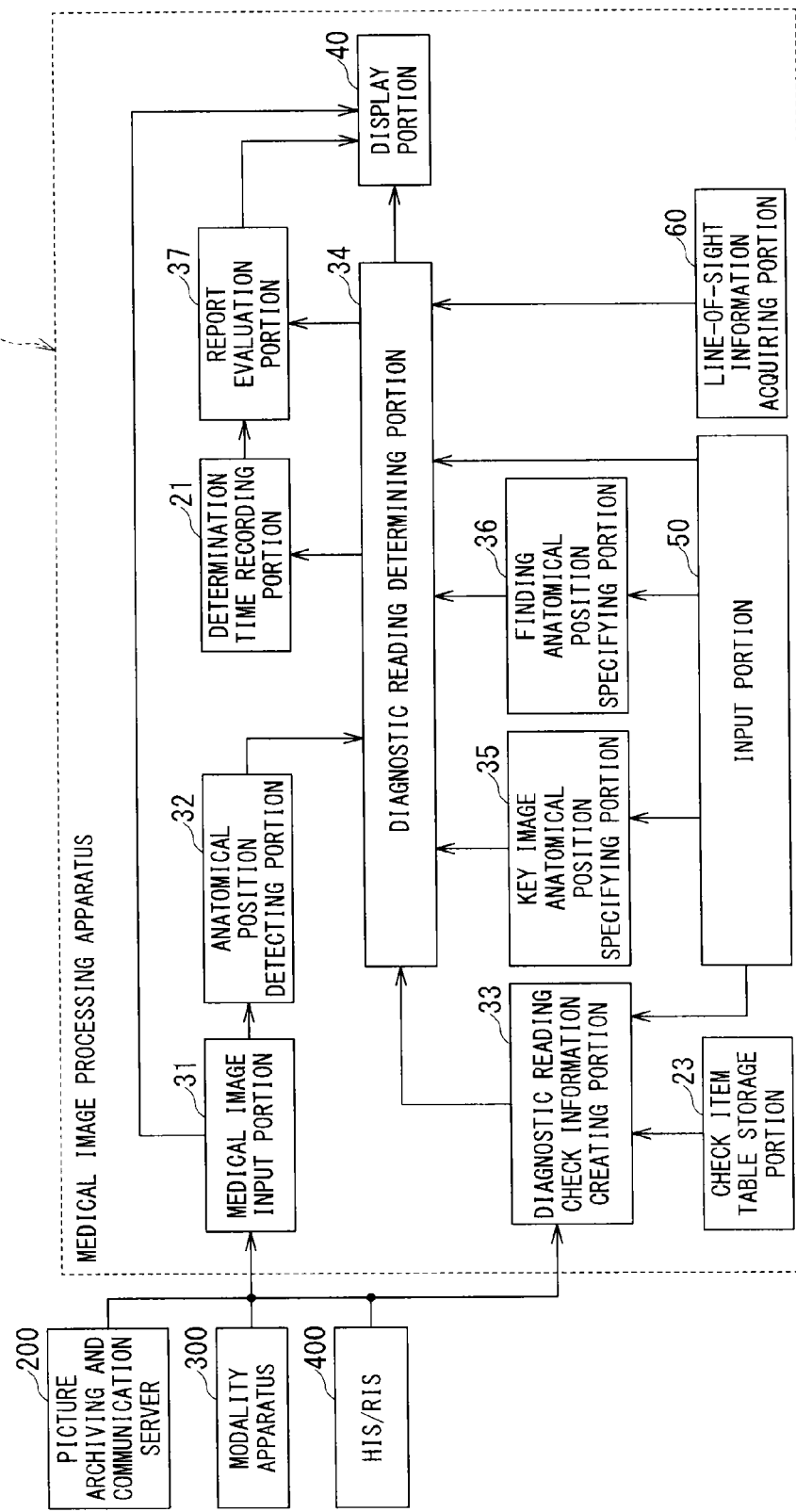
FIG. 2 is a functional block diagram illustrating a functional configuration example of the medical image processing apparatus according to the embodiment.

FIG. 2 is a functional block diagram illustrating a functional configuration example of the medical image processing apparatus 100 according to the embodiment. As illustrated in FIG. 2, the medical image processing apparatus 100 has a determination time recording portion 21, a check item table storage portion 23, a medical image input portion 31, an anatomical position detecting portion (position detecting portion) 32, a diagnostic-reading check information creating portion (check information determining portion) 33, a diagnostic reading determining portion 34, a key-image anatomical position specifying portion 35, a finding anatomical position specifying portion 36, a report evaluation portion 37, the display portion 40, the input device 50, and the line-of-sight information acquiring portion 60. In the above-described configuration, each function of the medical image input portion 31, the anatomical position detecting portion 32, the diagnostic-reading check information creating portion 33, the diagnostic reading determining portion 34, the key-image anatomical position specifying portion 35, the finding anatomical position specifying portion 36, and the report evaluation portion 37 is a function realized when the program stored in the storage portion 20 is executed by a processor (processing circuitry) of the main control portion 30, for example. These functions may be realized by collaboration among a plurality of processors (processing circuitries) or may be realized by hardware logic such as a circuit without using a CPU. The display portion 40 has a function realized when the main control portion 30 executes the program stored in the storage portion 20 and a display function. The line-of-sight information acquiring portion 60 has a function of collecting line-of-sight information by a camera or the like and a compilation function of the line-of-sight information according to a slice number, a coordinate or the like realized by execution of a program stored in the storage portion 20 by the main control portion 30.

The medical image input portion 31 receives medical image data from the medical picture archiving and communication server 200 and the modality apparatus 300, for example. The medical image input portion 31 receives a plurality of pieces of medical image data. The medical image data may be stored in the storage portion 20 in advance through a portable storage medium or via a network. A plurality of medical images each composed of a plurality of images is input into the medical image input portion 31.

Each of the plurality of medical images may be a bundle of a plurality of images (slice images, for example) constituting the medical image or may be input into the medical image input portion 31 as volume data created based on the plurality of images (slice images, for example) constituting the medical image, for example. Alternatively, the volume data and a plurality of images which is source data of the volume data may be associated with each other and input into the medical image input portion 31 as single medical image data. If the volume data is input into the medical image input portion 31, the medical image data or medical image can read the volume data in the description below. If one or a plurality of images is selected/extracted from the plurality of images constituting the medical image, this one or a plurality of images may be an MPR image (Multi Planar Reconstruction image) created based on the volume data.

The anatomical position detecting portion 32 has a function of detecting a position of a characteristic local structure of a human body from the medical image. For example, the anatomical position detecting portion 32 detects an anatomical position of the medical image data and gives information relating to the detected anatomical position (hereinafter referred to as anatomical position information) to the medical image data. The anatomical position information is imparted to the medical image data in advance in some cases. For example, provision of the anatomical position information to the medical image data may be performed at timing when the image is acquired by the modality apparatus 300 or may be performed at timing when it is stored in the medical picture archiving and communication server 200. In that case, detection processing of the anatomical position in the anatomical position detecting portion 32 and impartation processing of the anatomical position information to the medical image data can be omitted. A method for detecting the anatomical position in the anatomical position detecting portion 32 will be described later.

The anatomical position information imparted to the medical image data may be held in a data format such as XML data or binary data, for example, in a state associated with corresponding medical image data. The medical image data is data conforming to the DICOM (Digital Imaging and Communication Medicine) format and may be held as supplementary information in the DICOM standard. Moreover, the medical image data can hold patient information such as name, sex, body built, age and the like of a patient and study information such as an inspection type, an inspection purpose, a type of modality apparatus and the like as the supplementary information.

The check item table storage portion 23 stores a check item table listing anatomical positions which are check items for each of the inspection types, inspection purposes, medical histories, assumed disease names, primary sites, sex of the object, and age of the object. The check item table is created based on medical information, case information, accumulated information of diagnostic reading reports and the like stored in an external recording apparatus, for example. The accumulated information of diagnostic reading reports is a database accumulating the diagnostic reading reports created in the past inspections. The medical information and the case information may be documents or information collected via networks or may be information stored in the storage portion 20 and the like in advance. The check item table stored in the check item table storage portion 23 will be described later.

The diagnostic-reading check information creating portion 33 has a function of determining check information indicating the local structure which should be checked. For example, the diagnostic-reading check information creating portion 33 creates diagnostic reading check information (check information) listing the anatomical positions which become diagnostic reading targets as check target anatomical positions in the anatomical positions detected from the medical images. The diagnostic reading check information may be stored in the storage portion 20 or the external storage apparatus in advance, and the diagnostic reading doctor and the like may select the diagnostic reading check information in accordance with the inspection type, the inspection purpose, the medical history, the assumed disease name, the primary site, sex or age of the object and the like. Alternatively, it may be so configured that the inspection type, the inspection purpose, the medical history, the assumed disease name, the primary site of the patient, sex or age of the object or the like is acquired from the supplementary information of the medical image or the study information, patient information and the like stored in the HIS/RIS 400 and the like and the diagnostic reading check information is automatically selected from the acquired information. Moreover, the diagnostic reading check information may be created by extracting the check target anatomical position from the check item table using supplementary information of the image, the inspection type, the inspection purpose, the medical history, the primary site or assumed disease name, sex or age of the object acquired from the HIS/RIS 400 or the like as a key. A method for creating the diagnostic reading check information will be described later.

The diagnostic reading determining portion 34 has a function of determining whether or not the local structure which should be checked indicated in the check information has been diagnostically read based on the position of the local structure detected from the medical image. For example, the diagnostic reading determining portion 34 determines whether or not the check target anatomical positions listed in the diagnostic reading check information have been diagnostically read based on the anatomical position detected from the medical image. Moreover, the diagnostic reading determining portion 34 reflects determination results in the diagnostic reading check information. Furthermore, the diagnostic reading determining portion 34 creates a diagnostic reading check situation as the determination result and displays it on the display portion 40. The diagnostic reading determining portion 34 creates a diagnostic reading determination table based on the diagnostic reading check information. The diagnostic reading determination table lists determination standards for determining whether or not the check target anatomical positions listed in the diagnostic reading check information have been diagnostically read. A method of determination in the diagnostic reading determining portion 34 will be described later.

The determination time recording portion 21 records time in determination of the diagnostic reading determining portion 34. For example, the determination time recording portion 21 records time when the determination is completed in the diagnostic reading determining portion 34. The determination time recording portion 21 may record time when the determination is started or time required for determination.

The key-image anatomical position specifying portion 35 specifies a key-image anatomical position which is an anatomical position relating to a key image selected from the medical image. The key image is an image determined by the diagnostic reading doctor to be a key of diagnostic reading in the plurality of images included in single medical image data, and one or a plurality of images is designated as a key image for the single medical image data. A method of specifying the key-image anatomical position in the key-image anatomical position specifying portion 35 will be described later.

The finding anatomical position specifying portion 36 specifies a found anatomical position which is an anatomical position relating to finding describing observed abnormality and the like for the medical image as a diagnostic reading target. The finding anatomical position specifying portion 36 analyzes wording indicating the part or the local structure described in the finding and specifies a related anatomical position. A method of specifying the finding anatomical position in the finding anatomical position specifying portion 36 will be described later.

The report evaluation portion 37 determines a diagnostic reading report creation state from the diagnostic reading check information updated in the diagnostic reading determining portion 34 during diagnostic reading and creates a report evaluation result. The report evaluation portion 37 lists check target anatomical positions which have not been diagnostically read in the diagnostic reading check information as the report evaluation result and notifies it to the user. The report evaluation portion 37 displays the diagnostic reading performance situation as the report evaluation results based on the result determined by the diagnostic reading determining portion 34.

(2) Operation

Figure 3:
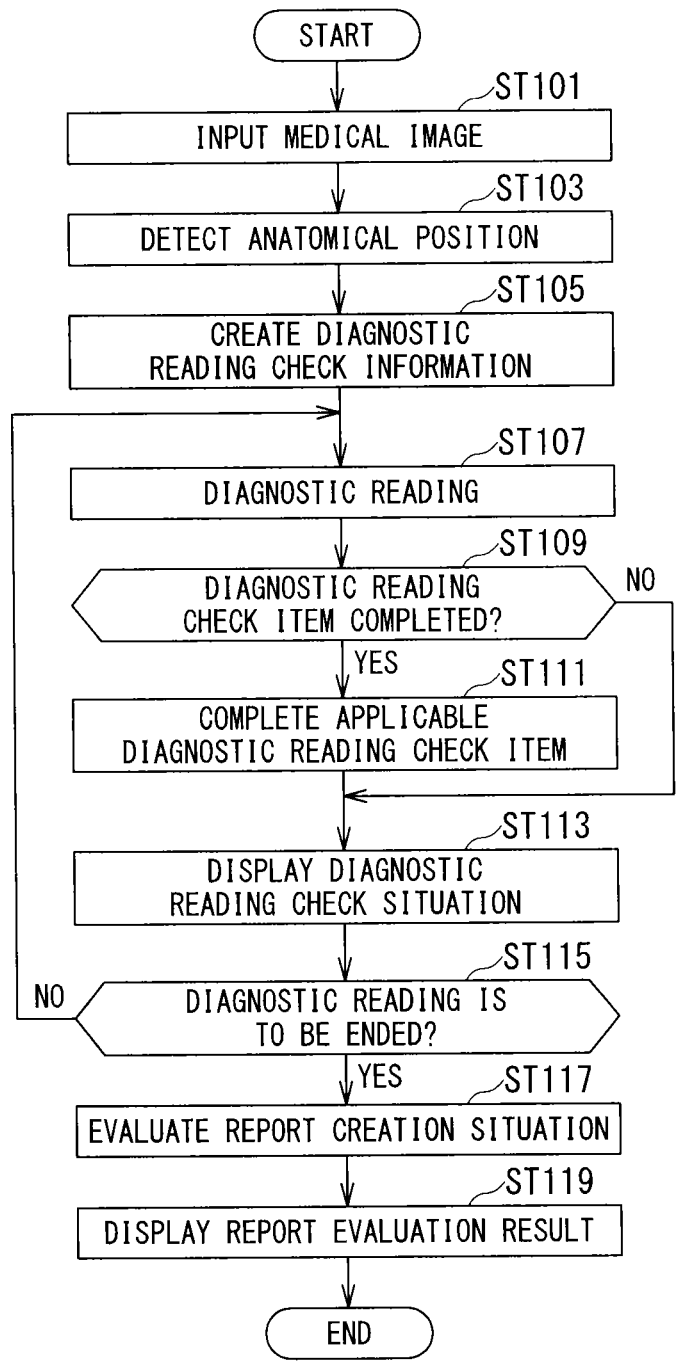
FIG. 3 is a flowchart illustrating an example of an operation of the medical image processing apparatus according to the embodiment.

FIG. 3 is a flowchart illustrating an example of an operation of the medical image processing apparatus 100 according to the embodiment.

At ST101, the medical image input portion 31 receives medical image data constituted by a plurality of images from the medical picture archiving and communication server 200 or the modality apparatus 300. This medical image data is volume data created based on the plurality of images (slice images, for example) constituting the medical image corresponding to the medical image data, for example. The volume data and a plurality of images which is a source data of the volume data may be associated with each other and input into the medical image input portion 31 as single medical image data.

At ST103, the anatomical position is detected by the anatomical position detecting portion 32 in the received medical image data.

Figure 4A:
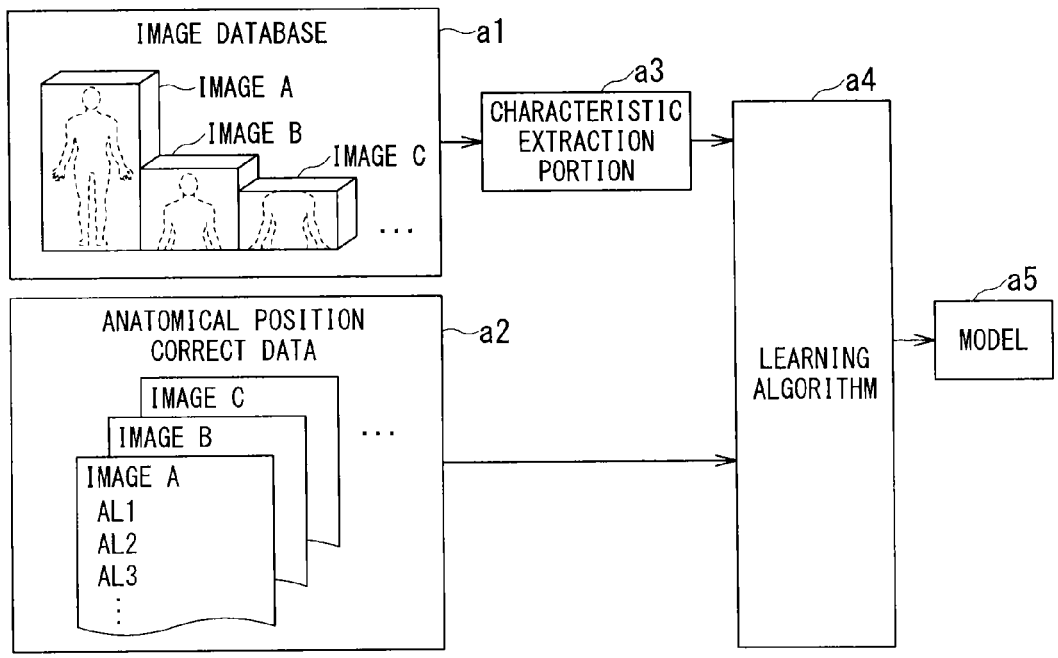
FIGS. 4A and 4B are views for explaining a detection method of the anatomical position.
Figure 4B:
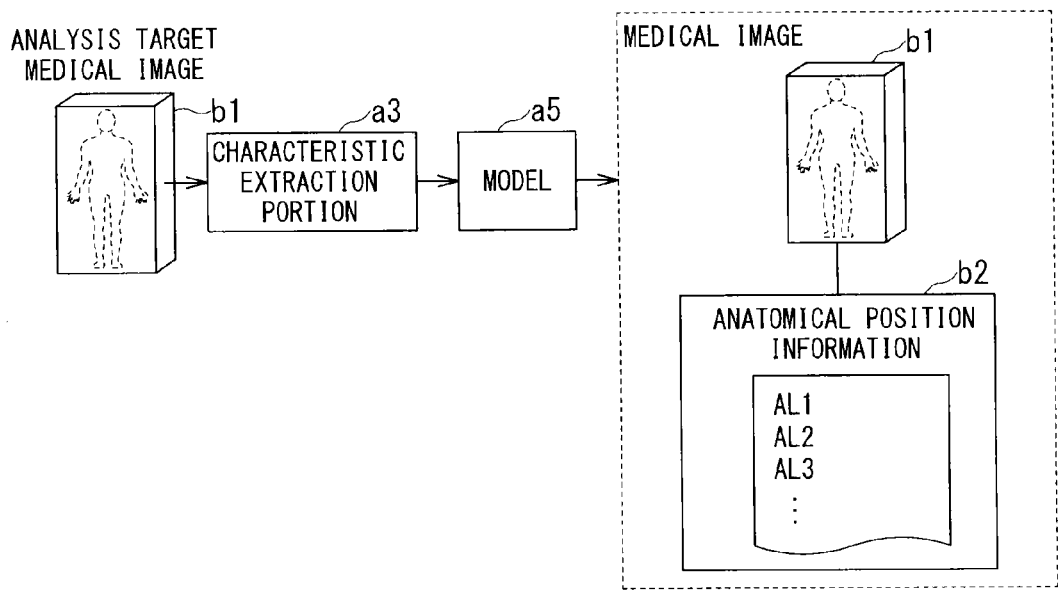

FIGS. 4A and 4B are views for explaining a detection method of the anatomical position. FIG. 4A illustrates an example of a method of creating a model a5 used for detection of the anatomical position. The model a5 illustrated in FIG. 4A may be stored in the storage portion 20 of the medical image processing apparatus 100 in advance or may be stored in an external storage apparatus.

As illustrated in FIG. 4A, the model a5 used in detection of the anatomical position is created by general machine learning or pattern recognition. FIG. 4A illustrates an example in which the model a5 is created by using an image database a1 and an anatomical position correct data a2. The image database a1 is a collection of volume data acquired by the X-ray CT apparatus or the MRI apparatus for the objects with different body shapes. As exemplified in FIG. 4A, the image database a1 includes not only the volume data (image A) of the entire body but also volume data (images B and C) picking up images of portions of a body. The anatomical position correct data a2 is data in which a correct anatomical position is determined in advance by experts such as doctors and the like for each of the images in the image database a1. As illustrated in FIG. 4A, a characteristic extraction portion a3 extracts a characteristic from the respective volume data of the image database a1 and creates the model a5 by learning algorithm a4 by using the anatomical position correct data a2.

The model a5 is used for associating the characteristics extracted from the image database a1 with the anatomical positions. This model a5 includes a model using machine learning, for example. Moreover, in such a model, different models according to sex, age, race, body build and the like may be created or the model may be able to absorb those differences.

FIG. 4B illustrates an example of processing executed in the anatomical position detecting portion 32. The anatomical position detecting portion 32 extracts the characteristics similarly to the characteristic extraction portion a3 in FIG. 4A and detects an anatomical position by using the model a5 having been already created for analysis target image data b1 whose anatomical position is unknown. More specifically, the anatomical position detecting portion 32 detects the local structure from the medical image and calculates a position in the medical image of the detected local structure as an anatomical position. Anatomical position information b2 calculated as above is imparted to the analysis target image data b1.

The above-described anatomical position can be detected by a mathematical statistic framework (calculation anatomical model) called calculation anatomy, not limited to the above-described method.

FIGS. 5A to 5D are views for explaining types of the local structures. The local structure is a characteristic structure of a human body playing an important role in understanding the medical image and is called AL (Anatomical Landmark) in some cases. For example, FIG. 5A illustrates an example of local structures of a head and a neck. FIG. 5A exemplifies an anterior arch (tubercle) of atlas (cervical vertebra I), an superior tip of dens/peg (cervical vertebra II), a superior aspect of right eye globe, a superior aspect of left eye globe, a center of right eye globe, and a center of left eye globe in order from above. Similarly, FIG. 5B exemplifies a bifurcation of trachea, a apex of right lung, a apex of left lung, an inferior angle of right scapula, an inferior angle of left scapula, a start of left subclavian artery (branching off aortic arch) for the local structures of a chest. FIG. 5C exemplifies a superior pole of right kidney, an superior pole of left kidney, a inferior pole of right kidney, an inferior pole of left kidney, a head of pancreas, and a tip of a tail of pancreas for the local structures of an abdomen. FIG. 5D exemplifies a lateral epicondyle of right femur, a medial epicondyle of right femur, a lateral epicondyle of left femur, a medial epicondyle of left femur, a lateral condyle of right tibia, and a medial condyle of right tibia for the local structures of a lower limb. The local structures are defined for the entire body at a grain size as illustrated in FIGS. 5A to 5D, for example, and a plurality of the local structures is determined for various bones, muscles, organs and the like constituting a human body. The anatomical positions are detected for each of these local structures.

Such anatomical positions are held in a state associated with the medical image data as anatomical position information. The anatomical position information is associated with IDs for uniquely identifying the medical images and the like, for example, and may be held as a database in the XML or text format in the storage portion 20 or the like or may be held integrally with the medical image data as supplementary information of the DICOM.

The anatomical position information can include part information such as the chest and the abdomen to which the local structures corresponding to the anatomical positions belong, body tissue information according to a functional system in a human body of the local structures corresponding to the anatomical positions such as an osseous system, a respiratory system and the like in addition to the information of anatomical positions.

Figures 6A, 6B:
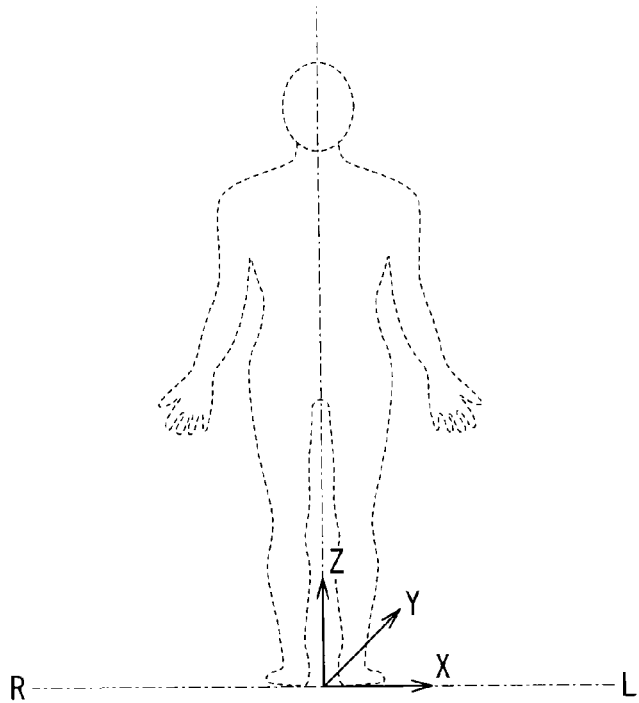
FIGS. 6A and 6B are views for explaining the anatomical position information.

FIGS. 6A and 6B are views for explaining the anatomical position information. A table in FIG. 6A illustrates an example of the anatomical position information. The table illustrating the anatomical position information in FIG. 6A indicates an identifier, a name, reliability, a part, a body tissue, and a position in a patient coordinate system (X-axis, Y-axis, Z-axis) of the anatomical position from the left. FIG. 6A exemplifies a part of the anatomical position information of the abdomen. The table in FIG. 6A indicates the identifier (ABDO25.C)), the name (center of body of L5), reliability (0.87), the part (abdomen), the body tissue (osseous system), and the patient coordinate system (X-axis (−3.1), Y-axis (23.4), Z-axis (90.0)) from the left. Similarly, a second stage indicates the identifier (ABDO32.C)), the name (superior aspect of right iliac spine), reliability (0.82), the part (abdomen), the body tissue (osseous system), and the patient coordinate system (X-axis (−11.1), Y-axis (−54.4), Z-axis (84.1)), and a third stage indicates the identifier (ABDO39.C)), the name (superior aspect of left iliac spine), reliability (0.83), the part (abdomen), the body tissue (osseous system), and the patient coordinate system (X-axis (−3.0), Y-axis (30.0), Z-axis (104.0)).

The identifier is an ID for uniquely identifying the anatomical position. The name indicates a name of the local structure and it is indicated by anatomical and medical specialized terms. Reliability is a numerical value indicating accuracy of the anatomical position. Since the anatomical position is data estimated by calculation through machine learning algorithm or pattern recognition, a numerical value indicating how accurate the position is calculated is imparted to each of the anatomical positions. In the example illustrated in FIG. 6A, it is indicated by numerical values from 0 to 1, and the closer to 1 the numerical value is, the higher reliability is indicated. The part indicates a part in a human body to which the local structure belongs and is classified as a chest and an abdomen, for example. The body tissue is classified in accordance with a function of the local structure and it is a neural system, an osseous system, a respiratory system or the like, for example. Such information relating to names of organs such as a heart, a lung, a femur and the like other than the part and the body tissue and a unit of anatomical structural bodies can be provided as anatomical position information. The patient coordinate system indicates the anatomical position by a coordinate of the X-axis, the Y-axis, and the Z-axis.

FIG. 6B is a view for explaining the patient coordinate system. As illustrated in FIG. 6B, the patient coordinate system is a coordinate system in which a right-and-left direction of a patient is the X-axis, a dorsabdominal direction of the patient is the Y-axis, and a capitopedal direction of the patient is the Z-axis. The X-axis increases in the right direction from a center of the patient, and the Y-axis increases in the back direction from the center of the patient as positive, while the Z-axis increases in a direction from the feet to the head of the patient. Such a patient coordinate system is depicted relatively by arbitrary positions such as a reference position of the volume data and the like.

The examples in FIGS. 6A and 6B illustrate an example of the information and the data format included in the anatomical position information.

Description will be made by returning to the flowchart in FIG. 3.

At ST105, the diagnostic-reading check information creating portion 33 creates the diagnostic reading check information relating to the medical image. The diagnostic reading check information is information listing the parts and local structures which should be diagnostically read as the check target anatomical positions based on the anatomical positions. The diagnostic reading check information may be set manually by the diagnostic reading doctor or the like, or the diagnostic reading check information set in advance may be selected. Alternatively, it may be automatically created from the check item table.

A method for creating the diagnostic reading check information from the check item table stored in the check item table storage portion 23 will be described below as an example by referring to FIGS. 7A to 7D and FIG. 8. The check item table is information listing the check target anatomical positions which become a basis of the diagnostic reading check information according to the types of inspections, the inspection purposes, the medical histories, the primary sites, sex and age of the object and the like. The check item table is a table listing the anatomical positions corresponding to the parts and the local structures requiring diagnostic reading in accordance with the types of the inspections such as medical examination and detailed examination for each part such as brain and a chest, for example. Hereinafter, the anatomical position (check target anatomical position) corresponding to the part or local structure requiring diagnostic reading shall be referred to as a "check target position".

FIGS. 7A to 7D are views for explaining an example of the check item table of the medical image processing apparatus 100 according to this embodiment.

A table exemplified in FIG. 7A illustrates a check item table indicating the anatomical positions corresponding to the parts and local structures which should be checked as check target positions for each inspection purpose. In the check item table, the check target positions are listed in accordance with an identifier or a local structure which can uniquely identify the anatomical position. The check item table exemplified in FIG. 7A shall be referred to as an inspection purpose table below. A first stage in the inspection purpose table in FIG. 7A shows four check target positions "AL1, AL3, AL5, AL7" for a "inspection purpose A". A second stage of the inspection purpose table in FIG. 7A shows three check target positions "AL2, AL4, AL6" for a "inspection purpose B" and similarly a third stage shows five check target positions "AL1, AL2, AL3, AL4, AL5" for a "check purpose C". If a specific disease such as a "lung cancer" is designated as an inspection purpose, for example, the diagnostic-reading check information creating portion 33 searches an applicable row in the inspection purpose table using the "lung cancer" as a key from the table exemplified in FIG. 7A, specifies the anatomical position to be a check target and makes it the diagnostic reading check information.

A table exemplified in FIG. 7B illustrates a check item table indicating the parts or the local structures which should be checked for each medical history as the check target positions. The check item table exemplified in FIG. 7B shall be referred to as a medical history table below. In the example in FIG. 7B, a first stage of the medical history table shows five check target positions "AL3, AL4, AL5, AL8, AL9" for a "medical history A". A second stage of the medical history table shows three check target positions "AL2, AL3, AL8" for a "medical history B", and a third stage shows four check target positions "AL1, AL2, AL3, AL6" for a "medical history C". A patient affected with pulmonary tuberculosis is said to be susceptible to a lung cancer or pneumonia statistically, for example. Therefore, in a case of a patient including pulmonary tuberculosis in the medical history, the anatomical positions relating to the lung cancer and pneumonia should be made check targets. The diagnostic-reading check information creating portion 33 can create the diagnostic reading check information with more accuracy by searching such medical history table in combination with the inspection purpose table.

A table exemplified in FIG. 7C illustrates a check item table indicating the parts or the local structures which should be checked for each assumed disease name as check target positions. The check item table exemplified in FIG. 7C shall be referred to as an assumed disease name table below. In the example in FIG. 7C, a first stage of the assumed disease name table shows three check target positions "AL5, AL6, AL7" for a "disease name A". A second stage of the assumed disease name table shows four check target positions "AL2, AL3, AL5, AL6" for a "disease name B", and a third stage shows two check target positions "AL1, AL5" for a "disease name C". For example, a disease name of a patient is forecast in advance through interview by a doctor or the like, and an inspection is conducted in order to check the forecast in some cases. When a disease name is forecast as above, the diagnostic-reading check information creating portion 33 may search the assumed disease name table and narrow the part or the local structure which should be diagnostically read into the diagnostic reading check information.

A table exemplified in FIG. 7D illustrates the parts or the local structures which are metastasis destinations or concurrence sites which should be checked for each anatomical position which is a primary site and a disease name as check target positions. A check item table exemplified in FIG. 7D shall be referred to as a primary site table below. In the example of the primary site table in FIG. 7D, the disease name and the anatomical positions corresponding to the metastasis destinations or concurrence sites in the case of the primary site "AL1" are illustrated. A first stage of the primary site table shows one check target position "AL9" for a "disease name A". A second stage of the primary site table shows three check target positions "AL5, AL6, AL7" for a "disease name B", and a third stage shows two check target positions "AL7, AL8" for a "disease name C". There are parts and local structures where probabilities of metastasis or concurrence are statistically high in relation to the disease corresponding to the inspection purpose, medical history, assumed disease name and the like. For example, in the case of the "lung cancer", the primary site is a lung but it is likely that the cancer metastasizes to parts or local structures such as brain or various bones. In the case of a patient having the "lung cancer" in the medical history, even if the inspection purpose is not an inspection for the "lung cancer", a result obtained by searching such a primary site table may be included in the diagnostic reading check information by considering the probability of metastasis.

There may be a table listing the check target positions in accordance with sex and age of the object, life habits such as smoking and drinking, symptoms complained by a patient and the like other than the examples of the check item tables illustrated in FIGS. 7A to 7D. Rows such as sex and age of the object, life habits such as smoking and drinking, symptoms complained by a patient and the like may be added to the check item tables exemplifies in FIGS. 7A to 7D. The check item table exemplified in FIGS. 7A to 7D may be associated with sex and age of the object, life habits such as smoking and drinking, symptoms complained by a patient and the like, respectively.

The check item tables exemplified in FIGS. 7A to 7D, respectively, may be obtained by analyzing medical information including statistical information or case information, description of the past diagnostic reading reports and the like. A key for searching these check item tables may be input by the diagnostic reading doctor or the like through the input device 50 or may be automatically determined from the supplementary information of the input medical images or the like. For example, the diagnostic-reading check information creating portion 33 may acquire information on the inspection purpose, the assumed disease name, the medical history and the like stored in the HIS/RIS 400 from a patient ID or a patient name in the supplementary information of the input medical image and search the check item table using it as a key. Alternatively, the diagnostic-reading check information creating portion 33 may search the check item table by combining a plurality of obtained keys such as the inspection purpose, the assumed disease name, the medical history and the like.

Figure 8:
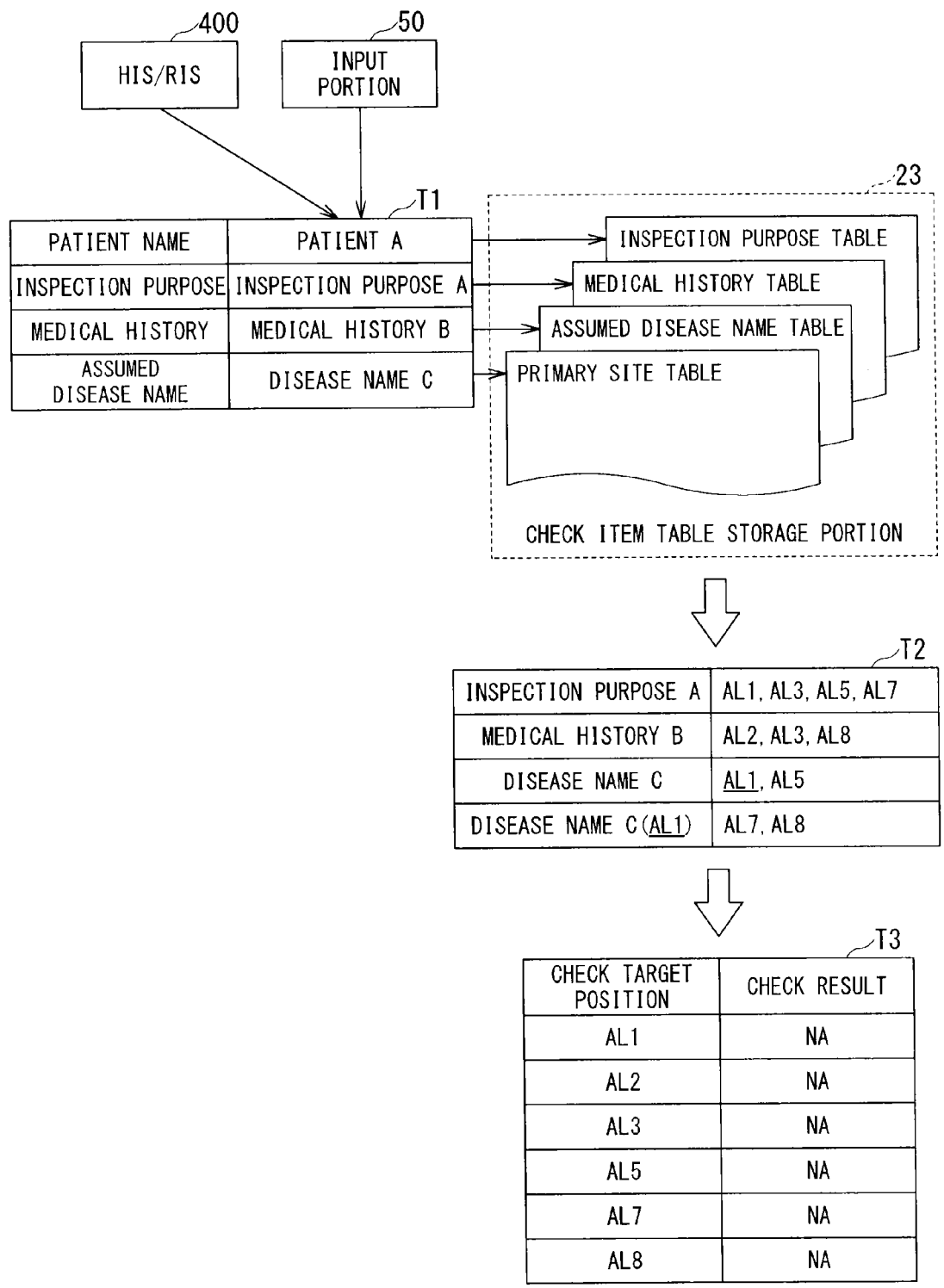
FIG. 8 is a view for explaining a method of creating the diagnostic reading check information of the medical image processing apparatus according to the embodiment.

FIG. 8 is a view for explaining a method of creating the diagnostic reading check information of the medical image processing apparatus 100 according to the embodiment. A table T1 illustrated in an upper portion in FIG. 8 shows patient information or study information of an object directly input from the input device 50 or automatically extracted from the study information or patient information stored in the HIS/RIS 400. For example, the table T1 may be created from the information obtained by searching the HIS/RIS 400 by using the patient name or study ID obtained from the supplementary information of the medical image data. The table T1 shows an inspection purpose A, a medical history B, and a disease name C for a patient A, for example. The diagnostic-reading check information creating portion 33 creates the diagnostic reading check information by using this information. The information shown in the table T1 may be any one of them or may be a combination.

A table T2 described in a middle stage in FIG. 8 illustrates a result obtained by searching the check item table using the information in the table T1 as a key. A first stage of the table T2 illustrates a result obtained by searching the inspection purpose table using the "inspection purpose A" as a key. Therefore, on the first stage of the table T2, the four check target positions "AL1, AL3, AL5, AL7" illustrated on the first stage of the inspection purpose table in FIG. 7A are shown. Similarly, a second stage of the table T2 illustrates a result obtained by searching the medical history table using the "medical history B" as a key. On the second stage of the table T2, the three check target positions "AL2, AL3, AL8" illustrated on the second stage of the medical history table in FIG. 7B are shown. A third stage of the table T2 illustrates a result obtained by searching the assumed disease name table using the "disease name C" which is the assumed disease name as a key. On the third stage of the table T2, the two check target positions illustrated on the third stage of the assumed disease name table exemplified in FIG. 7C are shown. A fourth stage of the table T2 illustrates a result obtained by searching the primary site table using the anatomical position "AL1" of the "disease name C" which is the assumed disease name as a primary site. On the fourth stage of the table T2, the check target positions "AL7, AL8" corresponding to the primary site "AL1" "disease name C" illustrated on the third stage of the primary site table exemplified in FIG. 7D are shown.

A table T3 illustrated on a lower stage in FIG. 8 illustrates an example of the diagnostic reading check information. A left column in Table T3 illustrates "AL1, AL2, AL3, AL5, AL7, AL8" obtained by excluding duplication of the check target positions extracted into Table T2 in FIG. 8 and by putting the rest in order. A right column in Table T3 exemplifies a column of a check result. The check result displays results of determination on whether or not the extracted check target positions have been diagnostically read. In the example in Table T3, "NA" is displayed in the check result of the diagnostic reading check information created in the diagnostic-reading check information creating portion 33. The check result may have a blank initial state, or an initial input value may be determined as in Table T3. In the example in Table T3, a state in which the check has not been completed (unchecked state) is indicated by a character string of "NA" but it may be indicated by numerals or symbols.

The determination processing in the diagnostic reading determining portion 34 using the diagnostic reading check information created as above will be described by returning to the flowchart in FIG. 3.

At ST107, the medical image is diagnostically read. In the diagnostic reading, a slice image selected by the diagnostic reading doctor and the like is displayed on the display portion 40. Moreover, in the diagnostic reading, operations including imaging processing such as enlargement, reduction, rotation, parallel movement, movement, gradation processing and the like applied to the displayed slice image, input of findings from the input device 50 provided with a keyboard and the like, selection of a key image corresponding to the finding from inside the displayed slice image and the like are performed.

At ST109, the diagnostic reading determining portion 34 creates the diagnostic reading determination table from the diagnostic reading check information and determines whether or not the diagnostic reading has been completed from the operation having been performed in the diagnostic reading based on the created diagnostic reading determination table.

At ST111, the diagnostic reading determining portion 34 updates the check result of the check target position determined that the diagnostic reading has been completed to "completed".

At ST113, the diagnostic reading check situation is displayed on the display portion 40.

A method for determining various ways of diagnostic reading in the diagnostic reading determining portion 34 will be described below by referring to FIGS. 9 to 14.

Figure 9:
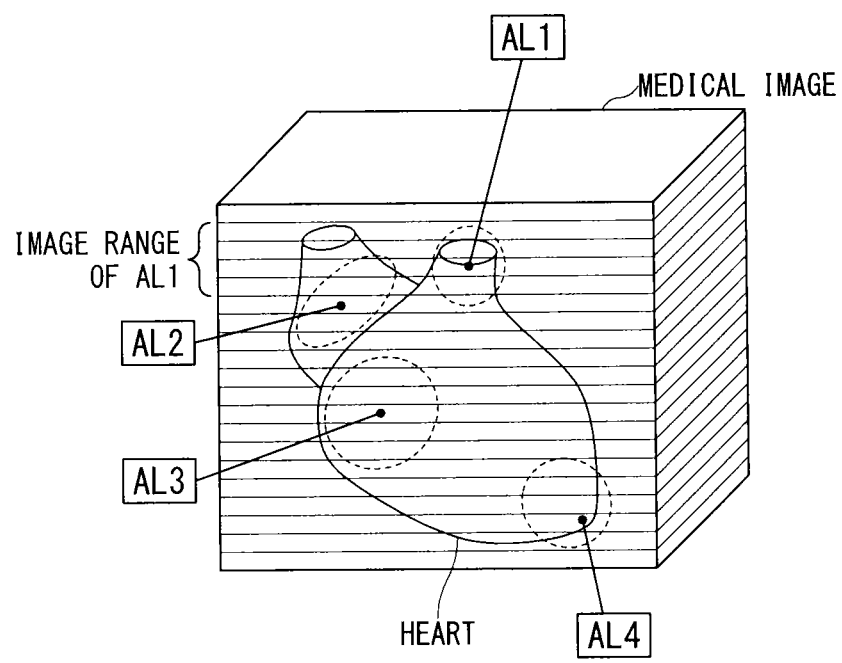
FIG. 9 is a view for explaining the slice image relating to the check target position of the medical image processing apparatus according to the embodiment.
Figures 10A, 10B:
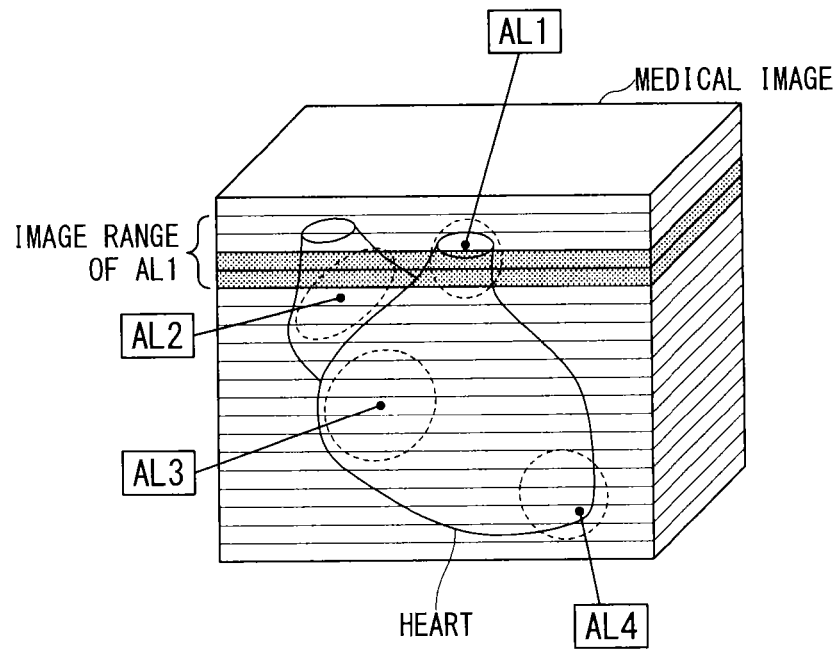
FIGS. 10A and 10B are views for explaining a diagnostic reading determination method based on display of an image of the medical image processing apparatus according to the embodiment.

Examples in FIG. 9 and FIGS. 10A and 10B explain a method of making diagnostic reading determination based on whether or not the slice image relating to the check target position is displayed on the display portion.

FIG. 9 is a view for explaining the slice image relating to the check target position of the medical image processing apparatus 100 according to the embodiment. FIG. 9 illustrates an example of medical image data including a heart. As described in FIGS. 6A and 6B, the anatomical position indicates a position of a characteristic local structure in a human body. However, as illustrated in FIG. 9, local structures corresponding to the anatomical position are present in a certain range around the anatomical position. For example, assuming that "AL1" is an anatomical position indicating a left coronary artery inlet portion, an actual left coronary inlet portion is not only a point indicated by a position of "AL1" but is a three-dimensional local structure in a range indicated by a broken line and has a spatial spread. Therefore, a slice image requiring diagnostic reading for the local structure corresponding to AL1 is a slice image including the range indicated by the broken line surrounding AL1

FIGS. 10A and 10B are views for explaining a diagnostic reading determination method based on display of an image of the medical image processing apparatus 100 according to the embodiment. The diagnostic reading determining portion 34 creates a diagnostic reading determination table listing slice images corresponding to the parts and local structures requiring diagnostic reading. The diagnostic reading determining portion 34 determines whether or not the part or local structure requiring diagnostic reading has been diagnostically read based on whether or not the slice image listed in the diagnostic reading determination table is displayed on the display portion 40.

FIG. 10A exemplifies the medical image similar to that in FIG. 9. A slice image indicated by shading indicates a slice image displayed on the display portion 40. On the other hand, a slice image without shading indicates a slice image not displayed on the display portion 40. FIG. 10A illustrates an example in which a part of the slice images corresponding to "AL1" is shaded and all the slice images corresponding to "AL1" are not displayed on the display portion 40.

A table illustrated in FIG. 10B is an example of the diagnostic reading determination table created by the diagnostic reading determining portion 34. The diagnostic reading determining portion 34 creates a table listing determination standards for determining whether or not the diagnostic reading has been completed as a diagnostic reading determination table for each of the check target positions listed in the diagnostic reading check information. The diagnostic reading determination table is added with the diagnostic reading determination standards to each of the check target positions of the diagnostic reading check information. The table exemplified in FIG. 10B indicates a slice number in the medical image corresponding to the check target position and presence of display indicating whether or not the image corresponding to the slice number is displayed on the display portion 40 in addition to the diagnostic reading check information. Assuming that the uppermost slice image in FIG. 10A has a slice number No. 1, the slice numbers of the slice images corresponding to AL1 are Nos. 2 to 5. The example of the diagnostic reading determination table in FIG. 10B shows "2, 3, 4, 5" as the slice numbers corresponding to the check target position "AL1". Similarly, in the example in the diagnostic reading table in FIG. 10B shows "4, 5, 6, 7" as the slice numbers corresponding to the check target position "AL2".

The slice image indicated by shading in FIG. 10A is a slice image that can be determined by the diagnostic reading determining portion 34 to be displayed on the display portion 40. Therefore, the diagnostic reading determining portion 34 updates the column indicating presence of display in FIG. 10B to "Yes" for the slice Nos. 4 and 5 indicated by shading in FIG. 10A. Similarly, the slice images of the slice Nos. 4 and 5 in "AL2" are also "Yes" in the column indicating presence of display. On the other hand, the other slice images are not displayed on the display portion 40, and thus, the diagnostic reading determining portion 34 enters "No" for presence of display. As described above, the diagnostic reading determining portion 34 updates the items of the diagnostic reading determination table and finally determines whether or not diagnostic reading of the check target position has been completed. In the example in FIG. 10B, the slice images corresponding to "AL1" are not extensively checked. Therefore, the diagnostic reading determining portion 34 determines that diagnostic reading has not been completed for "AL1" and displays "NA" as the check result. For example, when the slice Nos. 2 and 3 are displayed on the display portion 40, the diagnostic reading determining portion 34 can determine that the slice images corresponding to "AL1" have been extensively checked and can change the check result of "AL1" to "completed". On the other hand, since the slice numbers corresponding to "AL2" are Nos. 4 to 7, the check result of "AL2" is kept to be "NA".

In the examples in FIGS. 9 and 10A and 10B, the range of the slice images corresponding to the check target position is specified based on the size or range of the part or local structure, but a range of the slice images may be determined in accordance with reliability of the anatomical position information. For example, in a case of an anatomical position with low reliability, a region having an allowance of some more slices may be set outside the range of the anatomical position.

FIGS. 10A and 10B illustrate the example in which whether or not diagnostic reading has been completed is determined based on whether or not all the slice images corresponding to the check target position are displayed on the display portion 40. For example, there may be such a check target position that the check target position is weighted and determined that diagnostic reading is completed if only a part of the slice number extracted on the diagnostic reading determination table is displayed on the display portion 40.

As described above, in the example in FIGS. 10A and 10B, the determination method by the diagnostic reading determining portion 34 using presence of display of the slice image as a determination standard is illustrated, but the diagnostic reading determining portion 34 can make determination whether or not diagnostic reading of the check target position is completed using determination standards such as enlargement/reduction, gradation change, rotation, parallel movement, image processing or selection of a certain range in the slice image or a fact that a cursor or a pointer is positioned in a certain range in the slice image in addition to display of the slice image.

Figures 11A, 11B:
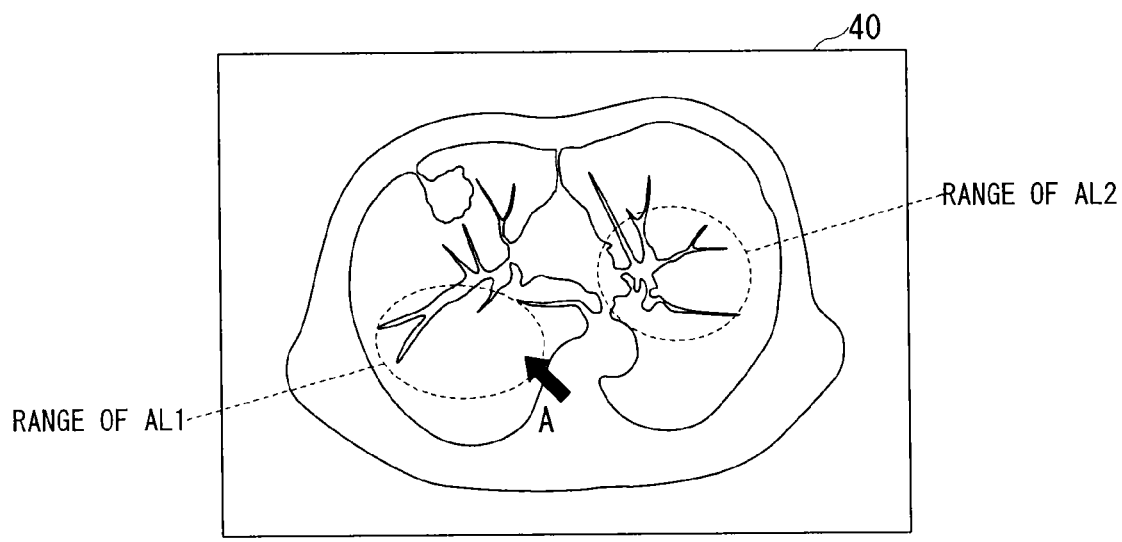
FIGS. 11A and 11B are views for explaining a method for determining diagnostic reading based on selection of a coordinate of the medical image processing apparatus according to the embodiment.

FIGS. 11A and 11B are views for explaining a method for determining diagnostic reading based on selection of a coordinate of the medical image processing apparatus 100 according to the embodiment. FIG. 11A illustrates a slice image displayed on the display portion 40. In the example in FIG. 11A, a region surrounded by a broken line on the left side of the slice image indicates a region corresponding to the check target position (AL1). Similarly, a region surrounded by a broken line on the right side of the slice image in FIG. 11A indicates a region corresponding to the check target position "AL2".

In the example in FIG. 11A, an arrow A is indicated in the range of AL1. The arrow A indicates a cursor or a pointer input through the input device 50. In the example in FIG. 11A, the diagnostic reading determining portion 34 acquires an operation that the user moves the cursor or the pointer on the slice image as above and makes determination.

The example in FIG. 11B illustrates a diagnostic reading determination table created by the diagnostic reading determining portion 34. In the example in 11B, coordinates sampled for the region on the slice image corresponding to the check target position are illustrated. The coordinates may be some typical coordinates of the regions on the slice image corresponding to the check target position or may be a coordinate of a center or a coordinate of a profile. In the example of FIG. 11B, three coordinates (X1, Y1), (X2, Y2), and (X3, Y3) are indicated in the diagnostic reading determination table as coordinates corresponding to the check target position "AL1". Similarly, two coordinates (X4, Y4) and (X5, Y5) are indicated as the coordinates corresponding to "AL2". The diagnostic reading determining portion 34 acquires an operation such that the cursor or the pointer has passed the coordinate illustrated in FIG. 11B or the coordinate is pressed by an input from the input device 50 and determines presence of selection. In the example of FIG. 11B, since the operation from the input device 50 for the coordinates (X1, Y1), (X2, Y2), and (X3, Y3) which are coordinates corresponding to "AL1" is checked, the diagnostic reading determining portion 34 makes diagnostic reading determination that the check result of "AL1" is "completed".

In the example in FIGS. 11A and 11B, the diagnostic reading determining portion 34 makes the check result of "AL1" "completed" when selection of all the sampled coordinates becomes "Yes", but the check result may be made "completed" when selection of one or more coordinates becomes "Yes". The determination on whether or not the cursor or the pointer has been moved may be made by the unit of cell obtained by dividing the screen into some parts instead of the unit of coordinate. For example, it may be so configured that the screen is divided into 16 cells, and whether or not the cursor or the pointer has passed the cell including the check target position is made the determination standard.

In FIGS. 11A and 11B, the example in which determination is made on whether or not the diagnostic reading is completed based on movement of the cursor or the pointer to a specific coordinate on the screen is illustrated. The diagnostic reading determining portion 34 may use not only the movement of the cursor or the pointer as above but also presence of an operation of enlargement, reduction, gradation processing, rotation, parallel movement, image processing and the like as a determination standard. For example, in diagnostic reading, the acquired image data is subjected to adjustment of a gradation value (contrast) of a pixel by display setting so that a part or a local structure as a diagnosis purpose can be observed easily. The image data acquired by the X-ray CT apparatus has a CT value for each of its pixels. This CT value is associated with an X-ray attenuation coefficient of a tissue, and assuming that the CT value of water is 0, that of air is −1000, and that of a bone is +1000, gradation characteristics are within a CT-value range of −1000 to +1000. For example, when a lung field is observed, since the lung field has many regions containing air, observation is made by gradation tuned to a low CT value. At that time, since a heart, a soft tissue of a chest wall or a bone has a high CT value, a signal is saturated, and observation cannot be made. As such, an intended part or local structure cannot be observed in some cases unless observation is made at correct contract by adjusting a gradation value. Therefore, whether or not the gradation processing has been changed appropriately and a target part or local structure has been correctly observed can be made a determination standard depending on the check target position.

The diagnostic reading determining portion 34 may make determination based on line-of-sight information of a user who performs diagnostic reading other than the operation from the input device 50 as described above.

Figure 12:
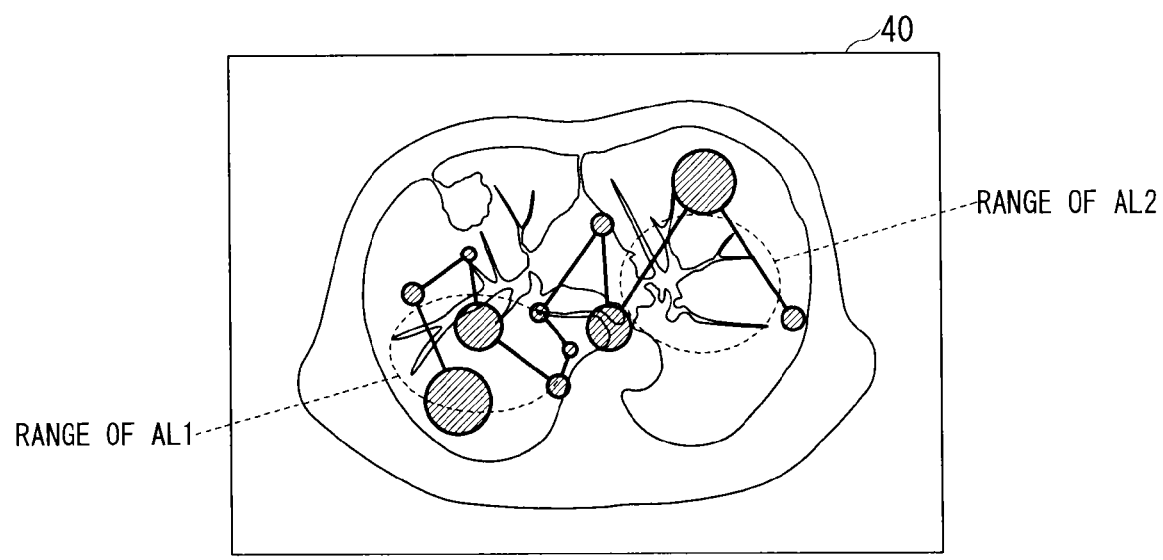
FIG. 12 is a view for explaining a method for determining diagnostic reading based on the line-of-sight information of the medical image processing apparatus according to the embodiment.

FIG. 12 is a view for explaining a method for determining diagnostic reading based on the line-of-sight information of the medical image processing apparatus 100 according to the embodiment. The line-of-sight information is acquired by the line-of-sight information acquiring portion 60 provided with a camera or the like. The line-of-sight information acquiring portion 60 can analyze the line-of-sight information of a diagnostic reading doctor or the like at a predetermined sampling interval and can aggregate it by the unit of slice images and coordinates.

In the example in FIG. 12, shaded circles indicate line-of-sight information of the diagnostic reading doctor and the like acquired by the line-of-sight information acquiring portion 60. A center position of the circle indicates a coordinate where the line-of-sight is located. A size of the circle indicates time during which the line-of-sight is maintained. A line connecting the circles indicates movement of the line-of-sight. Regions surrounded by a broken line indicate ranges of AL1 and AL2 which are the check target positions, respectively.

In the example of FIG. 12, the circles indicating the line-of-sight information concentrate in the range of AL1, and two circles having large diameters are indicated in the range of AL1. On the other hand, in the example in FIG. 12, no circle is indicated in a region of AL2. The diagnostic reading determining portion 34 may determine whether or not diagnostic reading of the check target position has been done from such line-of-sight information. For example, instead of the operation by using a cursor or a pointer illustrated in the example in FIGS. 11A and 11B, the line-of-sight information may be used. Moreover, determination may be made in accordance with a coverage of a line-of-sight in a region on the slice image corresponding to the check target position.

The diagnostic reading determining portion 34 may make determination based on a key image or an input content of finding when a diagnostic reading report is compiled.

Figures 13A, 13B:
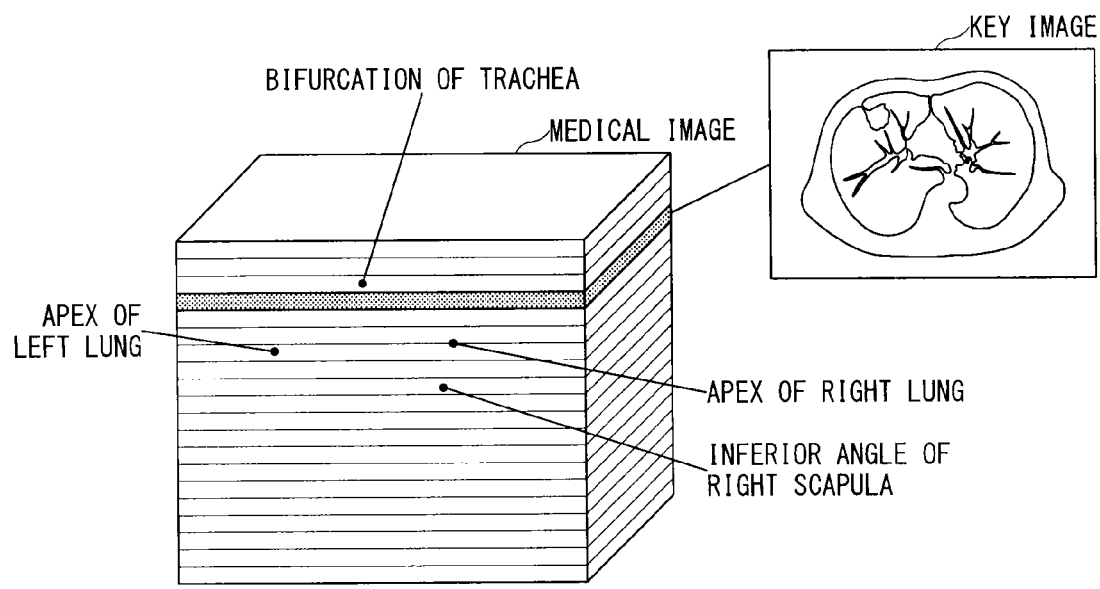
FIGS. 13A and 13B are views for explaining a method for determining diagnostic reading based on a key image of the medical image processing apparatus according to the embodiment.

FIGS. 13A and 13B are views for explaining a method for determining diagnostic reading based on a key image of the medical image processing apparatus 100 according to the embodiment. FIGS. 13A and 13B exemplify a method for determining whether or not the diagnostic reading has been made by using an anatomical position corresponding to the slice image selected as a key image.

The left side in FIG. 13A illustrates a medical image including a plurality of slice images, and FIG. 13A illustrates an example in which a slice image at a slice position indicated by shading is a slice image selected as a key image. In the vicinity of the slice image selected as the key image, a plurality of anatomical positions is present as illustrated in FIG. 13A.

FIG. 13B illustrates a list of anatomical positions present in the vicinity of the key image. The key-image anatomical position specifying portion 35 specifies an anatomical position located in the vicinity of the key image and creates a list of the key-image anatomical positions as illustrated in FIG. 13B. The key-image anatomical position may be an anatomical position within a predetermined distance from a center of the key image or may be specified in accordance with a part or an organ to which the closest anatomical position of the key image belongs, for example.

As described above, if there is an anatomical position corresponding to the check target position of the diagnostic reading check information among the key-image anatomical positions exemplified in FIG. 13B, the diagnostic reading determining portion 34 may determine the check result of the applicable check target position to be "completed".

The diagnostic reading determining portion 34 may check whether or not diagnostic reading of the diagnostic reading target AL has been done based on the anatomical position of an image to which annotation displayed in order to indicate a portion to be observed carefully on the image in creation of a diagnostic reading report is given.

Figure 14A:
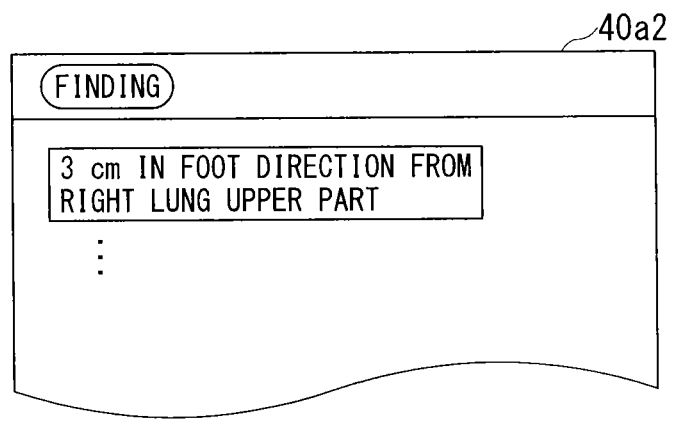
FIGS. 14A and 14B are views for explaining a method for determining diagnostic reading based on finding of the medical image processing apparatus according to the embodiment.
Figure 14B:
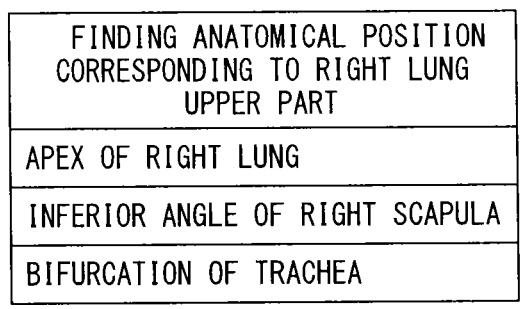

FIGS. 14A and 14B are views for explaining a method for determining diagnostic reading based on finding of the medical image processing apparatus 100 according to the embodiment. The finding is input from the input device 50. In an example in FIG. 14A, wording that "3 cm in the foot direction from right lung upper part" is entered in the finding. The finding anatomical position specifying portion 36 specifies a finding anatomical position exemplified in FIG. 14B from the wording.

The finding anatomical position specifying portion 36 extracts the wording corresponding to the part or local structure from the wording described in the finding, for example, and specifies the corresponding anatomical position by using general searching methods such as prefix search or dictionary search.

The finding anatomical position specifying portion 36 may also specify a finding anatomical position by analyzing contents spoken by the diagnostic reading doctor or the like from the input device 50 provided with a microphone or the like.

As described above, if there is an anatomical position corresponding to the check target position of the diagnostic reading check information in the finding anatomical positions exemplified in FIG. 14B, the diagnostic reading determining portion 34 may determine the check result to be "completed" for the applicable check target position.

The diagnostic reading determining portion 34 may perform diagnostic reading determination by using information stored in the determination time recording portion 21.

FIG. 15 is a view for explaining diagnostic reading determination time of the medical image processing apparatus 100 according to the embodiment. The determination time recording portion 21 stores time when diagnostic reading is started and time when the diagnostic reading is completed for the check target position. Time required until the diagnostic reading is completed may be calculated and stored.

In the example in FIG. 15, an example in which the diagnostic reading determining portion 34 makes determination based on presence of display of a slice image corresponding to the check target position is illustrated. In the example in FIG. 15, display start time when the slice image is displayed and display change time when the display is changed are indicated for each slice image corresponding to AL1. In the example in FIG. 15, a first stage indicates the diagnostic reading determination time (hour:minute:second) of a slice No. 2 corresponding to AL1, and the display start time of "15:16:20" and the display change time of "15:17:40" are indicated. Similarly, a second stage indicates the diagnostic reading determination time of a slice No. 3 corresponding to AL1, and the display start time of "15:17:40" and the display change time of "15:18:00" are indicated. A third stage indicates the diagnostic reading determination time of a slice No. 4 corresponding to AL1, and the display start time of "15:18:00" and the display change time of "15:19:10" are indicated. A fourth stage indicates the diagnostic reading determination time of a slice No. 5 corresponding to AL1, and the display start time of "15:19:10" and the display change time of "15:19:55" are indicated.

The determination time recording portion 21 acquires records of this display start time and display change time and determines and records time when the diagnostic reading is completed for AL1 In the example in FIG. 15, time when diagnostic reading of all the slice images corresponding to AL1 is completed is the display change time of the slice No. 5 at "15:19:55". Therefore, in the example in FIG. 15, "15:19:55" is stored as the check completion time of the "AL1".

The determination time recording portion 21 records diagnostic reading start time (the display start time in the example in FIG. 15). Therefore, the diagnostic reading determining portion 34 may determine whether or not the diagnostic reading has been performed in accordance with time required for the diagnostic reading. For example, in the example in FIG. 15, for how many minutes the diagnostic reading has been performed can be calculated for each of the slice images corresponding to AL1. If the diagnostic reading has been performed for a period of time not less than a threshold value (1 minute or more, for example), it may be determined that the diagnostic reading has been completed for the applicable slide image. Since a plurality of the slice images is specified as the slice images corresponding to AL1, determination if the diagnostic reading is completed may be made by using time obtained by integrating diagnostic reading time calculated for each of the plurality of slice images. A threshold value of the diagnostic reading time determined that the diagnostic reading is completed may be determined for each of the check targets AL.

As described above, a result determined in the diagnostic reading determining portion 34 is displayed on the display portion 40 as a diagnostic reading check situation (ST113).

Display of the diagnostic reading check situation will be described below in FIGS. 16 and 17A and 17B.

Figure 16:
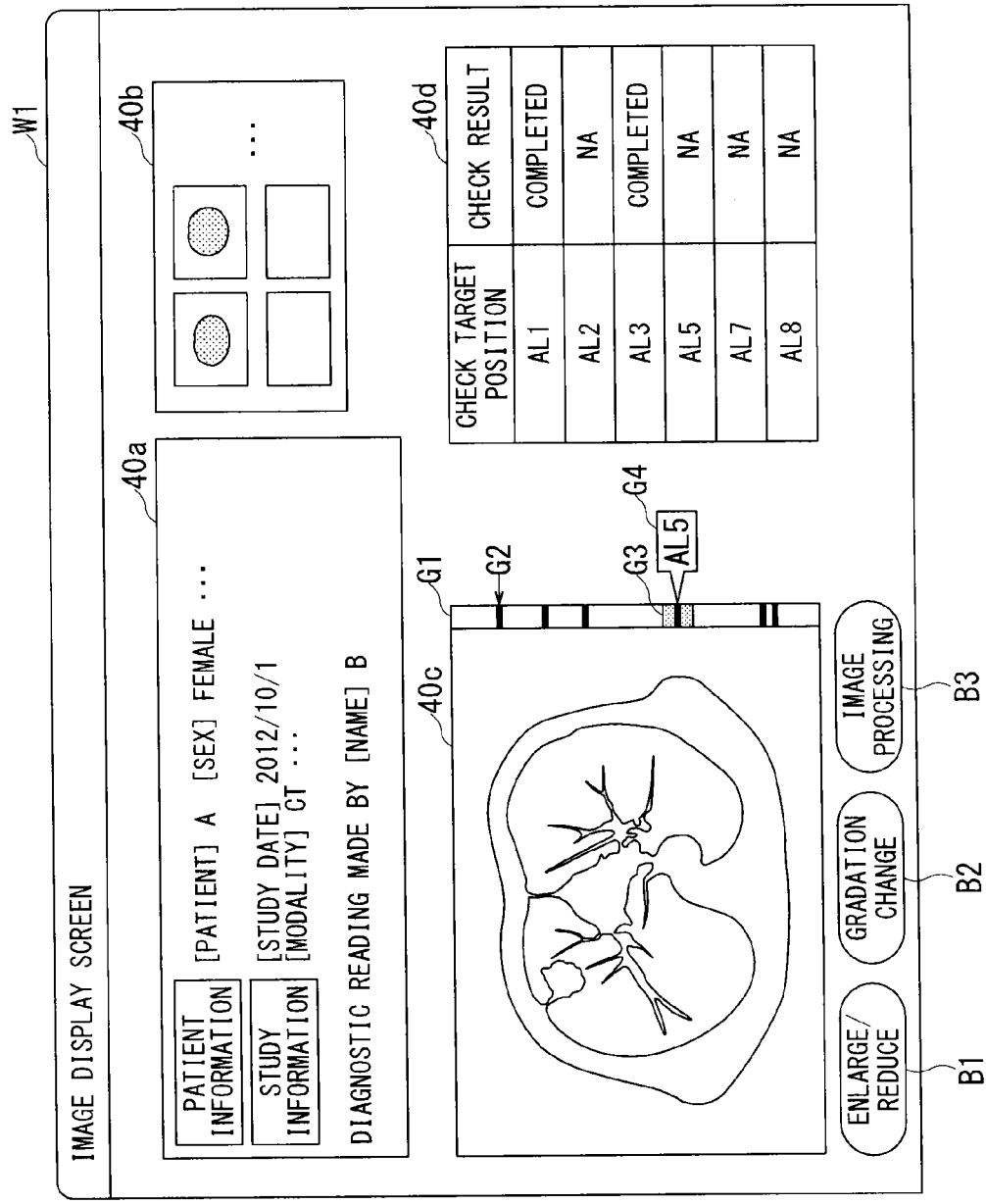
FIG. 16 is a view for explaining a display example of the diagnostic reading check situation of the medical image processing apparatus according to the embodiment.

FIG. 16 is a view for explaining a display example of the diagnostic reading check situation of the medical image processing apparatus 100 according to the embodiment. FIG. 16 illustrates an example of an image display screen W1 displaying a slice image in diagnostic reading. On the image display screen W1, a study information display region 40a displaying patient information, study information and the like relating to medical image data of a diagnostic reading target and an image thumbnail 40b displaying a plurality of slice images included in the medical image data on the medical image input portion 31 are displayed. In FIG. 16, a slice image display portion 40c displaying a slice image during diagnostic reading is illustrated on a lower part of the study information display region 40a. On the right side of the slice image display portion 40c, user interfaces such as a bar G1 corresponding to the number of all the slices in the medical image, a mark G2 indicating a check target position in the medical image, a slider G3 capable of displaying a slice image corresponding to preceding and succeeding slice numbers on the slice image display portion 40c by being moved vertically, a balloon G4 indicating the check target position during current diagnostic reading and the like are illustrated. On a lower part of the slice image display portion 40c, an "enlargement/reduction" button B1, a "gradation change" button B2, and an "image processing" button B3 are illustrated, respectively.

On a lower part of the image thumbnail 40b, a diagnostic reading check situation 40d is illustrated. The diagnostic reading check situation 40d exemplified in FIG. 16 is a table showing the check target position of the diagnostic reading check information exemplified in T3 in FIG. 8 and the check results. In the example in FIG. 16, "completed" is indicated in the check results of "AL1" and "AL3". This indicates that the diagnostic reading of "AL1" and "AL3" is determined by the diagnostic reading determining portion 34 to be completed. The check result may be a symbol or a checkbox.

The check result indicating whether or not the diagnostic reading has been completed may be overwritten by a diagnostic reading doctor or the like who is the user. For example, even if the diagnostic reading determining portion 34 automatically makes determination, if the diagnostic reading doctor or the like considers the diagnostic reading insufficient, change can be made by unchecking the checkbox or the like. In that case, the diagnostic reading determining portion 34 updates the check result from "completed" to "NA" in accordance with the change of the check result of the diagnostic reading check information.

FIGS. 17A and 17B are views for explaining other display examples of the diagnostic reading check situation of the medical image processing apparatus 100 according to the embodiment. FIGS. 17A and 17B illustrate a variation of the diagnostic reading check situation 40d exemplified in FIG. 16.

FIG. 17A is an example illustrating the check result in a ratio. For example, according to the diagnostic reading determination method for determining whether or not the diagnostic reading has been made by presence of display of the slice image, how many slice images have been checked in the slice images extracted as corresponding to the check target position can be calculated as a ratio in the total. Shading exemplified in FIG. 17A indicates such ratio and when the diagnostic reading is completed, a frame of the check result is totally shaded. By means of such display, a progress of the diagnostic reading of each of the check target positions can be indicated in accordance with the calculated ratio.

A shaded portion illustrated in FIG. 17A may indicate a length of time during which diagnostic reading is performed. By displaying time during which the diagnostic reading is performed for the respective check target positions, it can be used as an index indicating whether or not the diagnostic reading has been sufficiently performed.

FIG. 17B illustrates a result obtained by evaluating the check results in three stages accordance with the progress of the check for each of the check target positions. For example, display can be made such that the progress at 90% or more is determined to be favorable and displayed as "favorable", the progress at 50% or more and less than 90% to be an item requiring attention and displayed as "requiring attention", and the progress less than 50% to be insufficient diagnostic reading and determined to be "insufficient".

As described above, the diagnostic reading determining portion 34 determines whether or not the diagnostic reading has been completed, creates a diagnostic reading check situation which is the determination result and displays it on the display portion 40 for each of the check target positions.

The medical image processing apparatus 100 according to this embodiment can prevent a part or a local structure that should be diagnostically read from being missed by displaying such diagnostic reading check situation during the diagnostic reading. The progress of the diagnostic reading can be also grasped easily. Moreover, since the part or local structure that should be diagnostically read carefully is clearly indicated by an anatomical position, diagnostic reading can be performed flexibly, and efficient diagnostic reading is made possible. Moreover, whether or not the part or local structure that should be diagnostically read has been carefully rad and whether or not extensive diagnostic reading has been made can be evaluated for diagnostic reading by setting the diagnostic reading determination method. By digitalizing and the like a procedure in a work of diagnostic reading which is performed intuitively by using a diagnostic reading determination method or the like, a diagnostic reading doctor or the like who is a user can be made conscious of a method of diagnostic reading.

The display of the diagnostic reading check situation during diagnostic reading has been described. An operation when the diagnostic reading is completed will be described below by returning to the flowchart in FIG. 3.

At ST115, whether or not the diagnostic reading is to be finished is selected. End of the diagnostic reading is determined based on whether or not an operation such as closing of the diagnostic reading report displayed on the display portion 40 or printing or saving of the diagnostic reading report has been performed, for example.

At ST117, the report evaluation portion 37 evaluates a creation situation of a diagnostic reading report. The creation situation of the diagnostic reading report is determined based on a check result of the check target position in the diagnostic reading check information. The report evaluation portion 37 creates a report evaluation result according to the report creation situation. In the report evaluation result, contents are described such as a check target position of the diagnostic reading check information which has not been completed and a fact such that a diagnostic reading report cannot be finalized or saved, for example. The report evaluation result may describe a report creation order indicating how the diagnostic reading was performed or the like.

At ST119, a report evaluation result is displayed on the display portion 40.

Figures 18A, 18B, 18C:
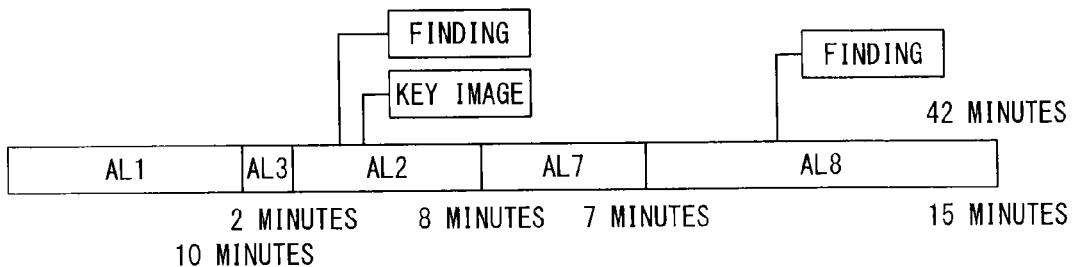
FIGS. 18A to 18C are views for explaining a display example of the report evaluation result of the medical image processing apparatus according to the embodiment.

FIGS. 18A to 18C are views for explaining a display example of the report evaluation result of the medical image processing apparatus 100 according to the embodiment. The report evaluation result is created by the report evaluation portion 37 when creation of the diagnostic reading is ended and displayed on the display portion 40.

FIG. 18A illustrates a display example of a report evaluation result in which an alarm message is described when there is an anatomical position determined by the diagnostic reading determining portion 34 that diagnostic reading has not been completed when diagnostic reading is finished. In the example in FIG. 18A, a report evaluation result displaying the anatomical positions which have not been diagnostically read in a list is displayed together with a message in a message window W2 to confirm that diagnostic reading has been performed. For example, if diagnostic reading is to be finished in a state of the diagnostic reading check situation 40d displayed on the image display screen W1 exemplified in FIG. 16, the anatomical positions which have been diagnostically read ("completed" is displayed) are only AL1 and AL3. Therefore, the report evaluation portion 37 determines from the diagnostic reading check information that diagnostic reading of all the check target positions has not been completed and creates a report evaluation result describing that fact. In the example in FIG. 18A, the report evaluation result displaying the AL2, AL5, AL7, and AL8 in a list as the anatomical positions which have not been diagnostically read is displayed in the message window W2.

FIG. 18B illustrates an example displaying a report evaluation result reporting how a diagnostic reading work has been performed when the diagnostic reading is finished. In the message window W2 exemplified in FIG. 18B, an example in which a diagnostic reading chart is added on the display example of the diagnostic reading check situation illustrated in the example in FIG. 17B is illustrated. The diagnostic reading chart illustrates an order of check of the check target positions and time in a bar graph. In the example of the diagnostic reading chart illustrated in FIG. 18B, a lateral axis indicates diagnostic reading time, and shading indicates timing at which the diagnostic reading is performed for the check target position and the time. From the diagnostic reading chart, work situations in the diagnostic reading such as the order of diagnostic reading, those subjected to the diagnostic reading work in parallel, a ratio of the respective diagnostic reading time of the anatomical positions in the entirety, timing of start or completion of the diagnostic reading and the like can be grasped. The shaded portion may display a portion whose check result changes from "needs attention" to "favorable" as a boundary in a different color, for example, or may visually display a site where work became stagnant.

FIG. 18C is a variation of FIG. 18B. Instead of the table illustrated in FIG. 18B, a view illustrated in FIG. 18C is displayed in the message window W2 as a report evaluation result. In the example in FIG. 18C, the respective diagnostic reading time of the anatomical positions is expressed by sizes of frames indicating the anatomical positions. The anatomical positions are arranged in the order in which the diagnostic reading is completed, and a label is displayed at the anatomical position at which a key image or finding has been input. By using such display, time required for the diagnostic reading, a diagnostic reading order or contents summarized in a report can be checked when the diagnostic reading report is finished.

As described above, when a diagnostic reading report creating work is to be finished, by displaying a report evaluation result exemplified in FIGS. 18A to 18C, a user can be prompted for a final check of the diagnostic reading report creation before actually printing or finalizing and saving the report. Moreover, by displaying a procedure of diagnostic reading, diagnostic reading time and the like, the diagnostic reading can be evaluated and feedback for the subsequent work can be made. By accumulating the procedure of the diagnostic reading work as above as a database, diagnostic reading methods of a skilled user can be shared with the others. In addition, by recording the diagnostic reading procedure, a missed site in diagnostic reading can be easily found, and when the diagnostic reading is resumed, duplicated work can be avoided, and improvement of efficiency and labor saving of the diagnostic reading work can be realized.

Second Embodiment

At ST105 in the first embodiment, the diagnostic-reading check information creating portion 33 creates the diagnostic reading check information relating to the medical image.

In a second embodiment, the diagnostic-reading check information creating portion (check information diagnostically read) 33 determines a display order of positions of detected local structures. In this case, the display portion 40 switches and displays a plurality of images (slice images, for example) constituting the medical image corresponding to the position of the local structure based on the determined display order.

For example, the diagnostic-reading check information creating portion 33 creates a diagnostic reading guide for determining the display order of the position of the local structure from a table stored in the check item table storage portion 23. In this case, the check item table storage portion 23 is assumed to have a diagnostic reading guide extraction table.

Specifically, the diagnostic guide extraction table stored in the check item table storage portion 23, the "diagnostic reading guide" corresponding to the "inspection purpose" is uniquely specified, and the "inspection purpose" is determined from the "part name" and the "disease name", for example, and the "diagnostic reading guide" corresponding to the "inspection purpose" is created.

The diagnostic reading guide extraction table is not limited to the "inspection purpose" relating to the "part name" and the "disease name" but the "inspection purpose" relating to the "organ name" and the "disease name" may be determined or the "inspection purpose" relating to the "part name", the "organ name", and the "disease name" may be determined.

As described above, the diagnostic-reading check information creating portion 33 searches the diagnostic reading guide extraction table stored in the check item table storage portion 23 and creates a diagnostic reading guide based on the inputs such as "part name", "patient name", "inspection purpose" and the like.

After the diagnostic-reading check information creating portion 33 creates the diagnostic reading guide corresponding to the inspection purpose, it determines a display order of the position of the local structure.

The diagnostic reading guide determines the display order of the position of the local structure based on at least one of a type of the inspection, a medical history, an assumed disease name, a primary site, age and sex of the object. For example, a diagnostic reading order and priority are assigned in advance for the diagnostic reading targets applicable to the position of the local structure for each of the diagnostic reading guide corresponding to the inspection purpose.

Then, the display portion 40 switches and displays a plurality of images (slice images, for example) corresponding to the position of the local structure based on the determined display order.

As described above, the display portion 40 displays the image of the diagnostic reading target corresponding to the position of the local structure in accordance with the diagnostic reading order or priority indicated in the diagnostic reading guide. Moreover, the display portion 40 changes the display order or skips those having been checked for diagnostic reading based on the diagnostic reading order and priority and displays the image of the diagnostic reading targets.

As a result, by diagnostically reading the medical image displayed on the display portion 40 in accordance with the display order, a user can diagnostically read the position of the local structure according to the order to be diagnostically read.

The diagnostic-reading check information creating portion 33 may associate at least one of the inspection purpose, past study information, and a disease name with information for determining the display order of the position of the local structure and store the diagnostic reading guide extraction table in the check item table storage portion 23.

Third Embodiment

In the first embodiment, the medical image processing apparatus 100 is configured to display the diagnostic reading check situation on the display portion 40 at Step ST113.

In the third embodiment, a position of a characteristic local structure of a human body is detected in each of a plurality of medical images and is displayed in association with the respective medical images. In this case, the medical image is constituted by a first medical image constituted by a plurality of images and a second medical image constituted by a plurality of images, for example. The medical image processing apparatus 100 displays the first medical image and the second medical image in association with each other.

As a result, in the third embodiment, a user can perform diagnostic reading of the second medical image while looking at the first medical image. The medical image processing apparatus 100 may display a plurality of images constituting the first medical image in association with a plurality of images constituting the second medical image.

For example, the anatomical position detecting portion (position detecting portion) 32 of the medical image processing apparatus 100 detects a position of a characteristic local structure of a human body from each of the first medical image and the second medical image.

The display portion 40 of the medical image processing apparatus 100 displays the first medical image and the second medical image with a slice image of the first medical image and a slice image of the second medical image in association with each other based on the positions of the respective local structures of the first medical image and the second medical image.

The display portion 40 can display the first medical image and the second medical image at the same time by associating the slice image of the first medical image and the slice image of the second medical image with each other based on the positions of the plurality of different local structures.

The display portion 40 may change a slice image of the second medical image in conjunction with a change of a slice position of the slice image of the first medical image and display it. In this case, the display portion 40 of the medical image processing apparatus 100 can display the slice image of the first medical image and the slice image of the second medical image at the same time.

As described above, the display portion 40 of the third embodiment displays the slice image of the first medical image in conjunction with the slice image of the second medical image based on the position of the local structure. That is, the display portion 40 can display the slice image of the first medical image and the slice image of the second medical image in synchronization with a page turning operation such as a display change speed and display change timing of the slice images.

The term of a "processor" or "processing circuitry" as described above includes, for example, a special purpose CPU (Central Processing Unit), a general purpose of CPU, ASIC (Application Specific Integrated Circuit), a PLD (Programmable Logic Device) including a SPLD (Simple Programmable Logic Device) and a CPLD (Complex Programmable Logic Device), and/or FPGA (Field Programmable Gate Array). The "processor" or "processing circuitry" implements the functions or processing as described above by executing one or more programs stored in one or more memories. Further, the functions or the processing described above may be implemented by a single "processor" or "processing circuitry", or may be implemented by plural "processors" or "processing circuitries".

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus displaying at least one medical image obtained by imaging an object, comprising:
   processing circuitry configured:
   to detect a position of a characteristic local structure of a human body from the medical image;
   to determine check information indicating the local structure which should be checked; and
   to determine whether or not the local structure which should be checked indicated in the check information has been diagnostically read based on the position of the local structure detected from the medical image; and
   a display configured to display a determination result.

2. The medical image processing apparatus according to claim 1, wherein
   the check information is determined based on the position of the local structure associated with at least one of a type of an inspection, a medical history, an assumed disease name, a primary site, an age of the object, and sex of the object.

3. The medical image processing apparatus according to claim 1, wherein the processing circuitry is configured to determine whether or not the position of the local structure which should be checked of each of the images relating to the position of the local structure which should be checked indicated in the check information in a plurality of images constituting the medical image has been diagnostically read.

4. The medical image processing apparatus according to claim 1, further comprising:
   an input device, wherein
   whether or not a position of the local structure which should be diagnostically read has been read is determined based on whether or not at least one image processing of enlargement, reduction, rotation, parallel movement, selection, and gradation processing was executed for each of the images relating to the position of the local structure which should be checked indicated in the check information in the plurality of images constituting the medical image.

5. The medical image processing apparatus according to claim 1, wherein the processing circuitry is further configured to acquire line-of-sight information of a user who creates a diagnostic reading report for the medical image, and whether or not the position of the local structure which should be checked indicated in the check information has been diagnostically read is determined based on the line-of-sight information.

6. The medical image processing apparatus according to claim 1, wherein the processing circuitry is further configured to select a key image from a plurality of images constituting the medical image and to specify a key-image anatomical position which is an anatomical position relating to the key image from the selected key image, and whether or not the position of the local structure which should be checked indicated in the check information has been diagnostically read is determined based on whether or not the key-image anatomical position is included in the position of the local structure which should be checked indicated in the check information.

7. The medical image processing apparatus according to claim 6, wherein
   the processing circuitry is further configured to specify an anatomical position relating to an image given with annotation; and whether or not the position of the local structure which should be checked indicated in the check information has been diagnostically read is determined based on whether or not the anatomical position relating to the image given with the annotation is included in the position of the local structure which should be checked indicated in the check information.

8. The medical image processing apparatus according to claim 6, wherein the processing circuitry is further configured to specify a finding anatomical position which is an anatomical position relating to a finding checked for the key image, and whether or not the position of the local structure which should be checked indicated in the check information has been diagnostically read is determined based on whether or not the finding anatomical position is included in the position of the local structure which should be checked indicated in the check information.

9. The medical image processing apparatus according to claim 1, wherein the processing circuitry is further configured to record time at determination of the diagnostic reading, and whether or not the position of the local structure which should be checked indicated in the check information has been diagnostically read is determined based on whether or not time required for the determination has exceeded a predetermined threshold value.

10. The medical image processing apparatus according to claim 9, wherein
    the predetermined threshold value is determined for each of the positions of the local structures which should be checked.

11. The medical image processing apparatus according to claim 1, wherein the processing circuitry is further configured to create a report evaluation result by determining a diagnostic reading report creation situation from a determination result of the local structure which should be checked, wherein the display displays the report evaluation result.

12. The medical image processing apparatus according to claim 1, wherein the processing circuitry is further configured to determine a display order of the position of the detected local structure; and
the display switches and displays a plurality of images constituting the medical image corresponding to the position of the local structure based on the determined display order.

13. The medical image processing apparatus according to claim 12, wherein
the display order of the position of the local structure is determined based on at least one of a type of an inspection, a medical history, an assumed disease name, a primary site, an age of an object, and sex of the object.

14. The medical image processing apparatus according to claim 12, further comprising:
a memory circuit configured to store at least one of an inspection purpose, past study information, and a disease name in association with information for determining the display order of the position of the local structure.

15. The medical image processing apparatus according to claim 1, wherein
the medical image is constituted by a first medical image constituted by a plurality of images and a second medical image constituted by a plurality of images;
the processing circuitry is configured to detect a position of the characteristic local structure of the human body from each of the first medical image and the second medical image; and
the display displays an image constituting the first medical image and an image constituting the second medical image in association based on the position of the local structure of each of the first medical image and the second medical image.

16. The medical image processing apparatus according to claim 15, wherein
the display displays the image constituting the first medical image and the image constituting the second medical image in association based on the positions of a plurality of the different local structures.

17. The medical image processing apparatus according to claim 15, wherein
the display changes and displays the position of the image constituting the second medical image in conjunction with a change of the position of the image constituting the first medical image.

18. A medical image processing system for acquiring at least one medical image obtained by imaging an object through a network, comprising:
processing circuitry configured:
to detect a position of a characteristic local structure of a human body from the medical image;
to determine check information indicating the local structure which should be checked; and
to determine whether or not the local structure which should be checked indicated in the check information has been diagnostically read based on the position of the local structure detected from the medical image; and
a display configured to display a determination result.

* * * * *